United States Patent
Giordani et al.

(10) Patent No.: US 7,824,710 B2
(45) Date of Patent: Nov. 2, 2010

(54) CRYSTALLINE AND STABLE FORM OF ANDOLAST

(75) Inventors: Antonio Giordani, Pavia (IT); Antonino Santoro, Monza (IT); Paolo Senin, Monza (IT); Matteo Ghirri, Milan (IT); Francesco Makovec, Lesmo (IT); Paola Gilotta, Monza (IT); Walter Peris, Milan (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 528 days.

(21) Appl. No.: 11/678,277

(22) Filed: Feb. 23, 2007

(65) Prior Publication Data

US 2007/0149586 A1 Jun. 28, 2007

(30) Foreign Application Priority Data

Apr. 10, 2006 (EP) .................................. 06112427

(51) Int. Cl.
*A61K 9/14* (2006.01)
*A61K 31/41* (2006.01)
*C07D 207/00* (2006.01)
(52) U.S. Cl. ........................ 424/489; 514/381; 548/250
(58) Field of Classification Search ................ 424/489; 514/381; 548/250
See application file for complete search history.

(56) References Cited

U.S. PATENT DOCUMENTS 5,976,576 A * 11/1999 Makovec et al. ............ 424/489

FOREIGN PATENT DOCUMENTS

| EP | 0 896 821 A1 | 2/1999 |
| EP | 1 634 595 A1 | 3/2006 |
| WO | 90/09989 A1 | 9/1990 |

OTHER PUBLICATIONS

Morissette et al., Advanced Drug Delivery Rev, vol. 56, 2004, pp. 275-300, especially p. 276.*
Brittain, Polymorphism in Pharmaceutical Solids, published 1999, pp. 1, 2 and 185.*
Makovec, F. et al., "Antiallergic and Cytoprotective Activity of New N-Phenylbenzamido Acid Derivatives", J. Med. Chem., 1992, pp. 3633-3640, vol. 35.
Persiani, S. et al., "Pharmacokinetics of Andolast after Administration of Single Escalating Doses by Inhalation in Mild Asthmatic Patients", Biopharm. Drug Dispos., 2001, pp. 73-81, vol. 22.
Revel, L. et al., "CR 2039, a new bis-(1H-tetrazol-5-yl)phenylbenzamide derivative with potential for the topical treatment of asthma", European Journal of Pharmacology, 1992, pp. 45-53, vol. 229.
Czuczwar, S.J. et al, "Influence of a potential anti-asthmatic drug, CR 2039, upon the anticonvulsive activity of conventional antiepileptics against maximal electroshock-induced seizures in mice", J. Neural Transm., 1996, pp. 1371-1379, vol. 103.
Atkins, P., "Dry Powder Inhalers: An Overview", Respiratory Care, Oct. 2005, pp. 1304-1312, vol. 50, No. 10, Daedalus Enterprises.
Singhal, D. et al., "Drug polymorphism and dosage form design: a practical perspective", Advanced Drug Delivery Reviews, 2004, pp. 335-347, vol. 56, Elsevier B.V.
ICH Guideline Q6A, 1999.
Newman, A.W. et al., "Solid-state analysis of the active pharmaceutical ingredient in drug products", Drug Discovery Today, Oct. 19, 2003, pp. 898-905, vol. 8, No. 19.
"X-Ray Diffraction", USP issue 23, National Formulary 18, 1995, pp. 1843-1844.
ICh Guideline Q3C, Jul. 17, 1997.

* cited by examiner

*Primary Examiner*—Susannah Chung
(74) *Attorney, Agent, or Firm*—Sughrue Mion, PLLC

(57) ABSTRACT

Described is a new crystalline Form A of Andolast disodium salt, triclinic, displaying a thermal event at 98-112° C. and melting with decomposition at about 400° C. (DSC). Andolast disodium Form A is a not hygroscopic solid, surprisingly stable to several humidity conditions in a temperature range acceptable for ordinary storage conditions. In addition its stability allows both chemical manufacturing and pharmaceutical manufacturing process consistency and reproducibility under conditions more viable and less expensive when compared to those used for highly hygroscopic solids.

15 Claims, 25 Drawing Sheets

Figure 1: XRPD Spectrum of Form A.
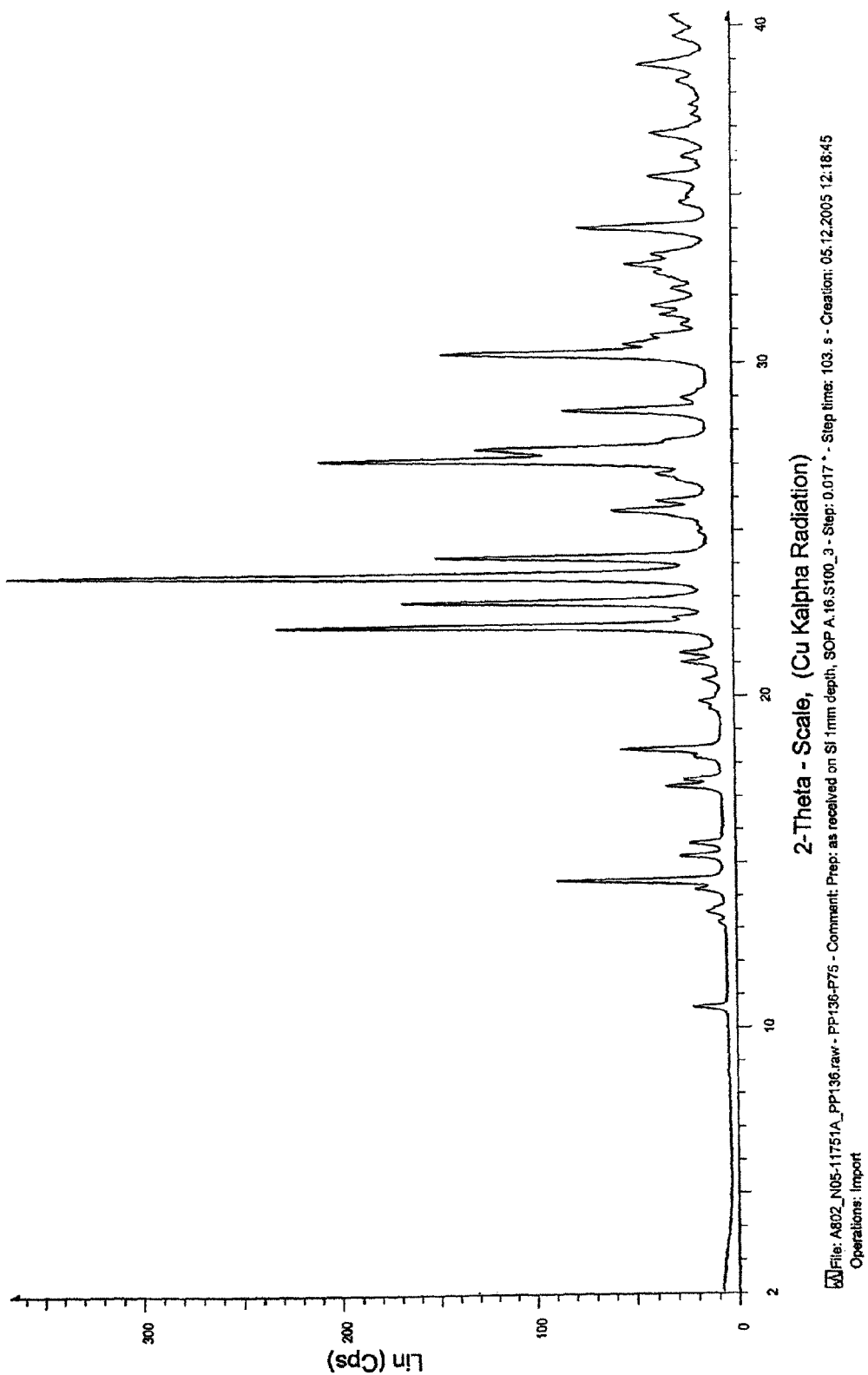

Figure 2: FT-IR spectrum of Form A.
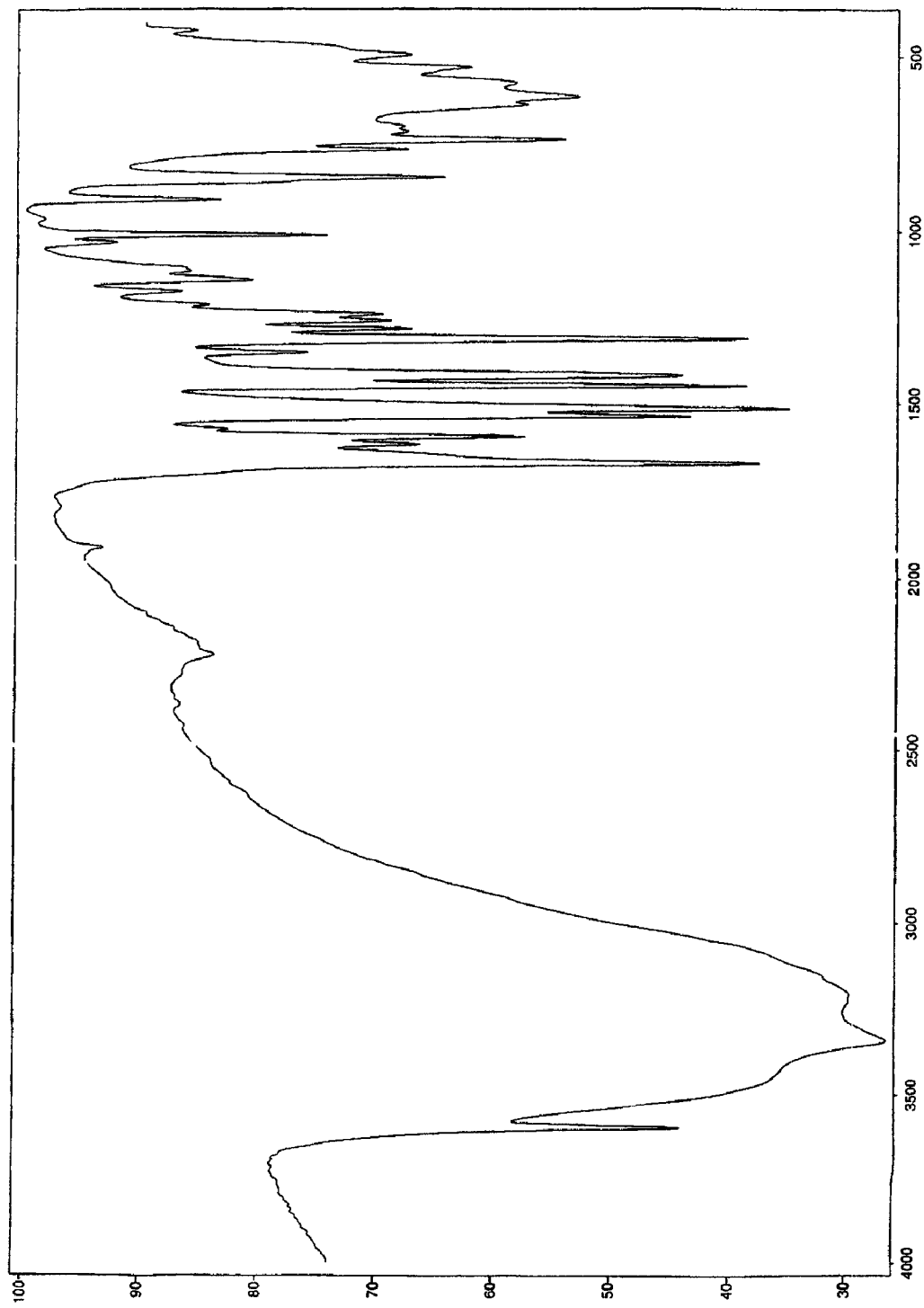

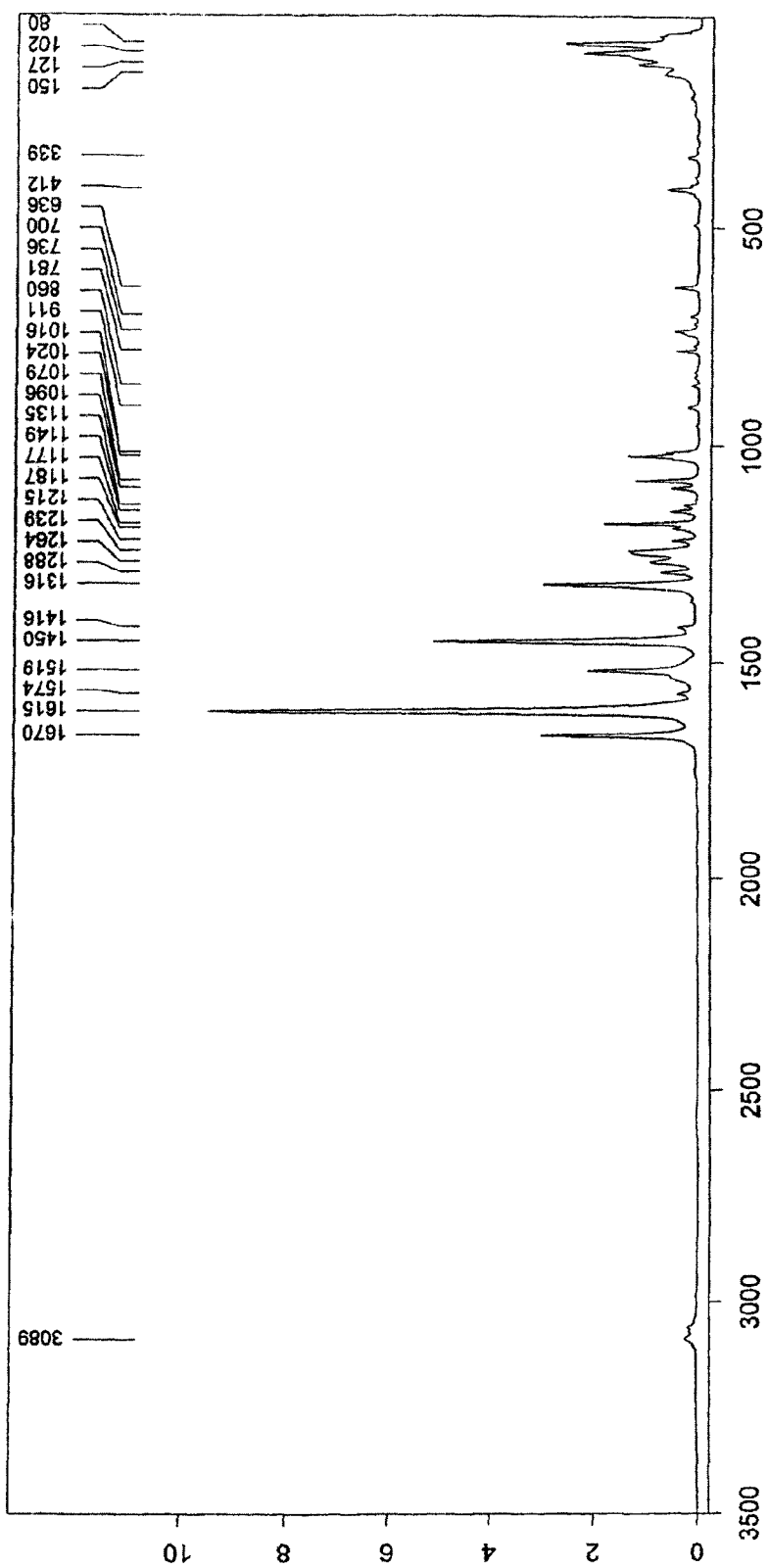
Figure 3: Raman Spectrum of Form A.

Figure 4a: XRPD Spectrum for Batch B/6272
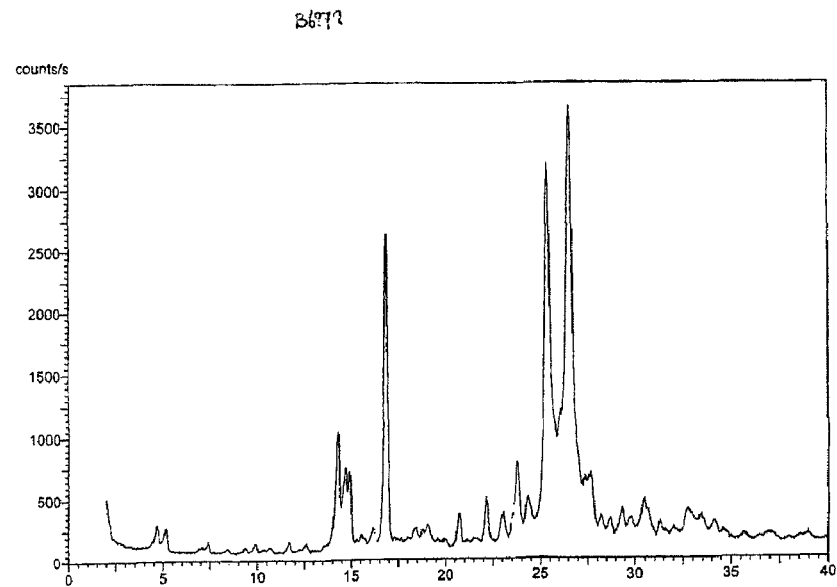
Figure 4b: XRPD Spectrum for Batch B/3610
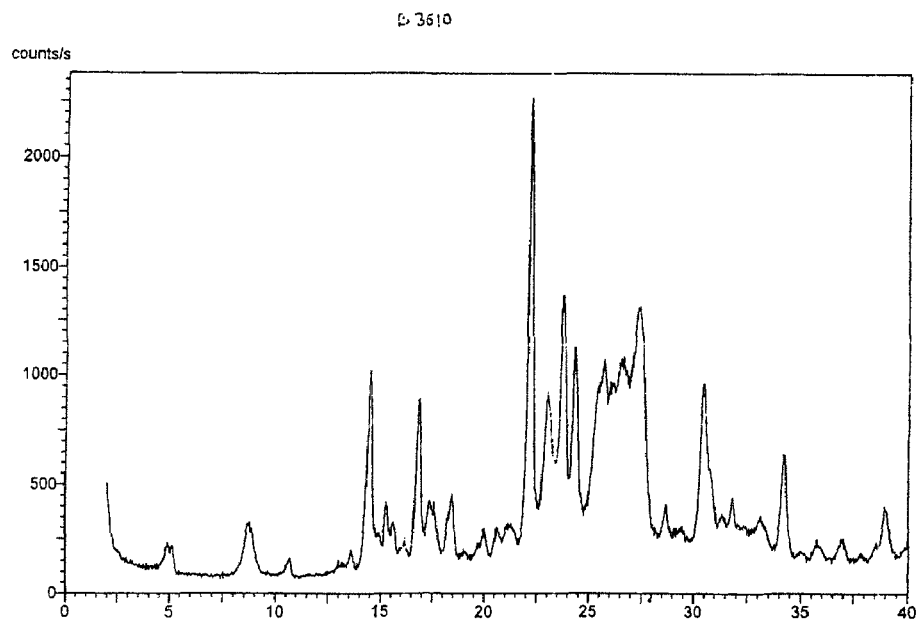

Figure 4c: XRPD Spectrum for Batch B/6981
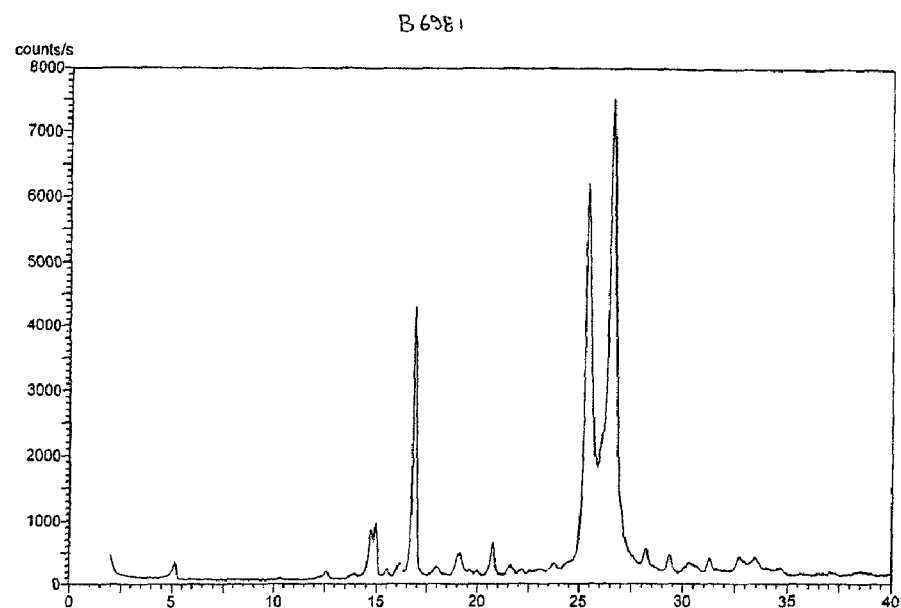
Figure 4d: XRPD Spectrum for batch B/7081
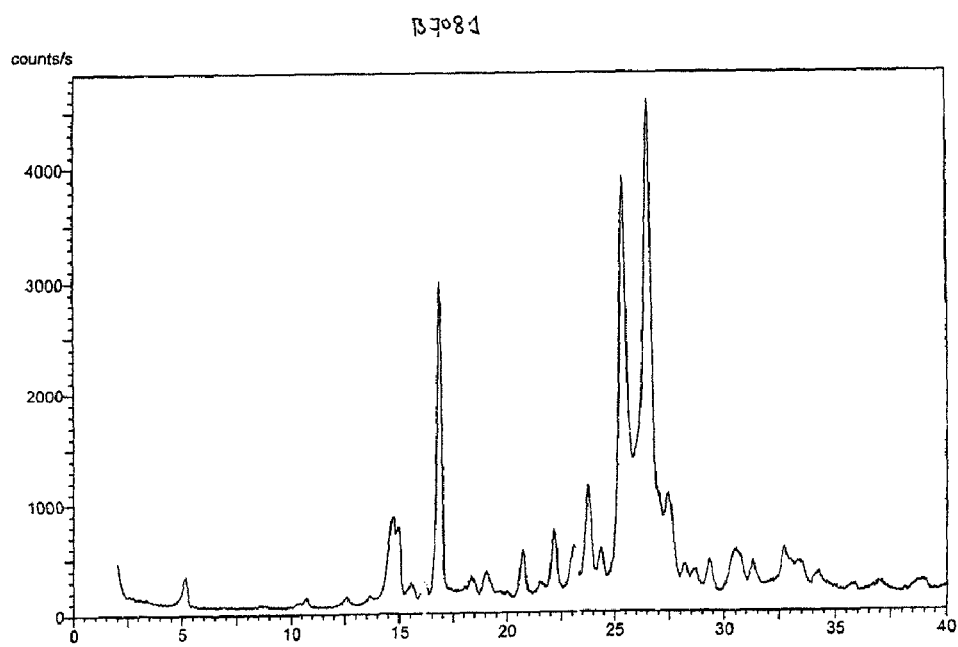

Figure 5a: FT-Raman spectrum for batch B/6272
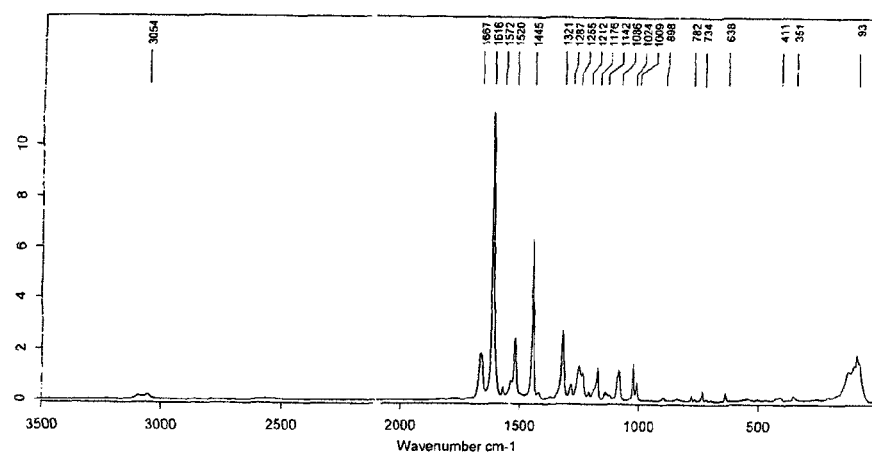
Figure 5b: FT-Raman spectrum for Batch B/3610
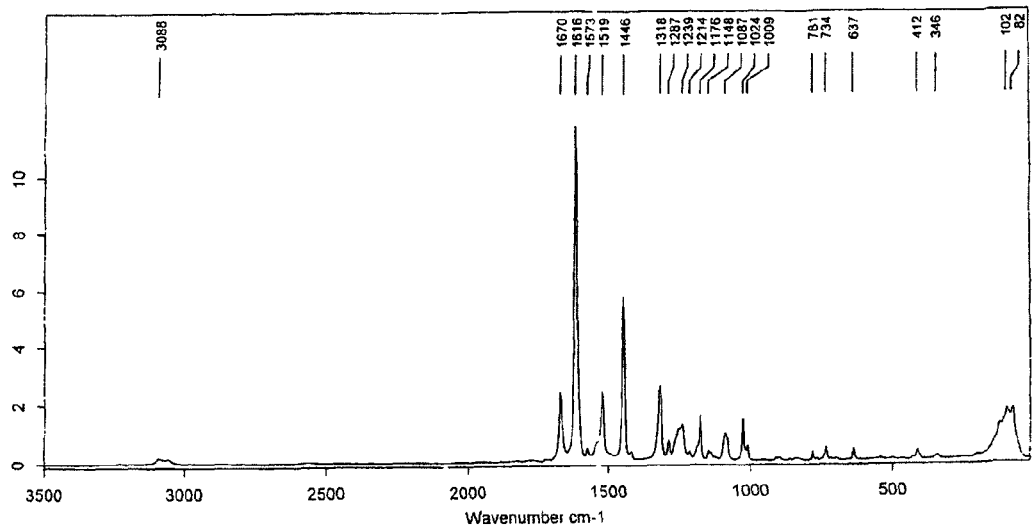

Figure 5c: FT-Raman spectrum for Batch B/6981
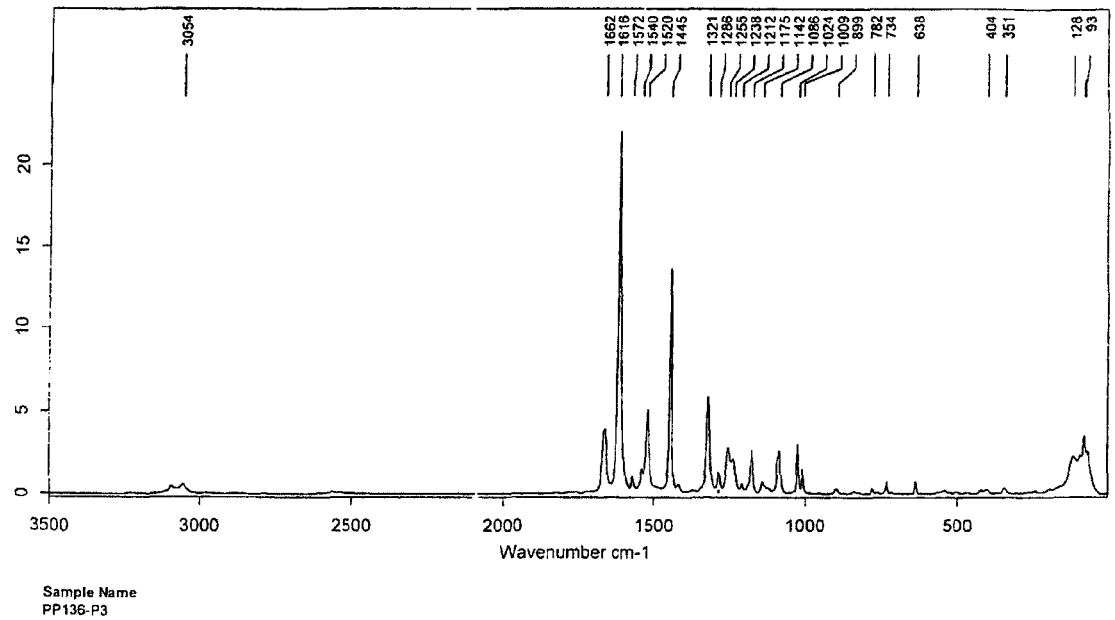
Figure 5d: FT-Raman spectrum for Batch B/7081.
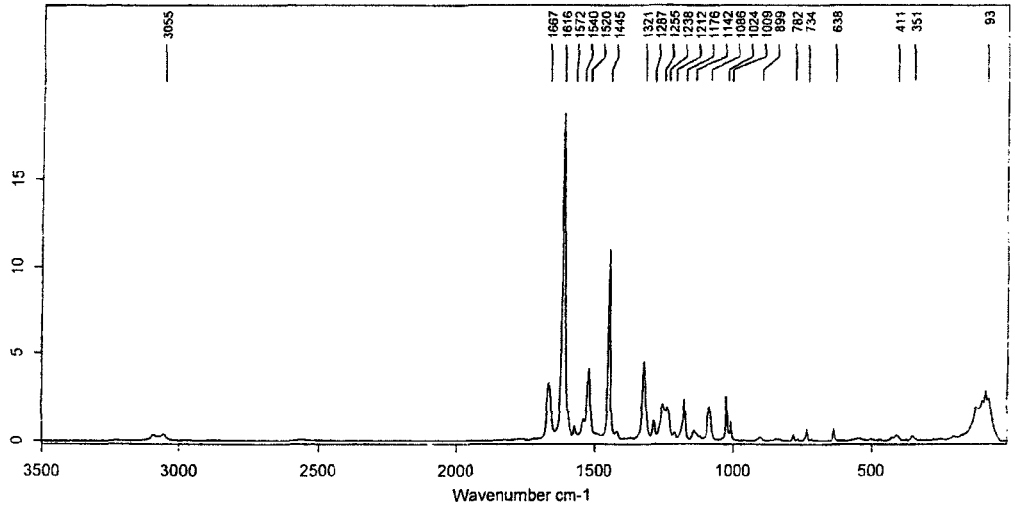

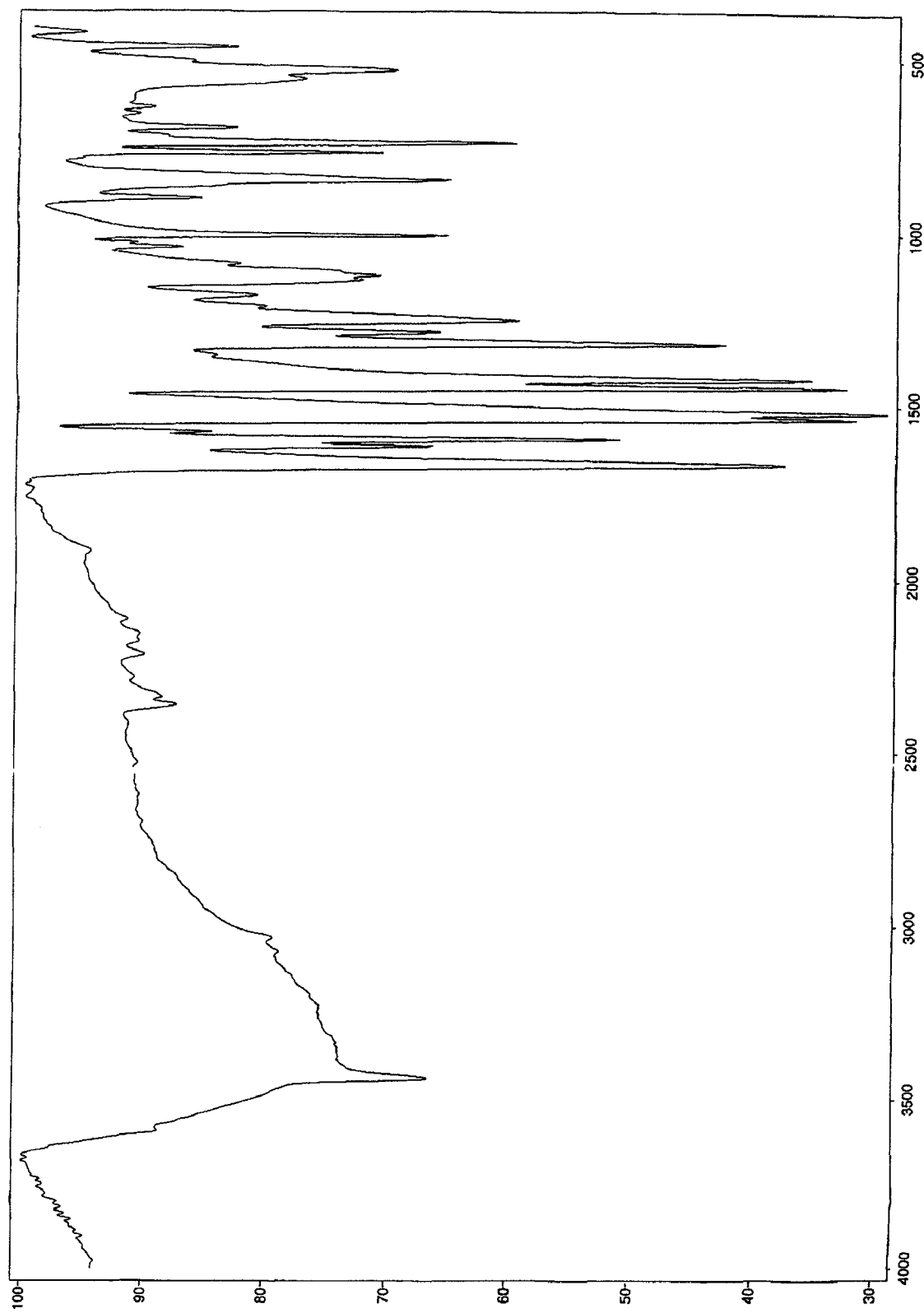
Figure 6a: FT-IR Spectrum of batch B/7080.

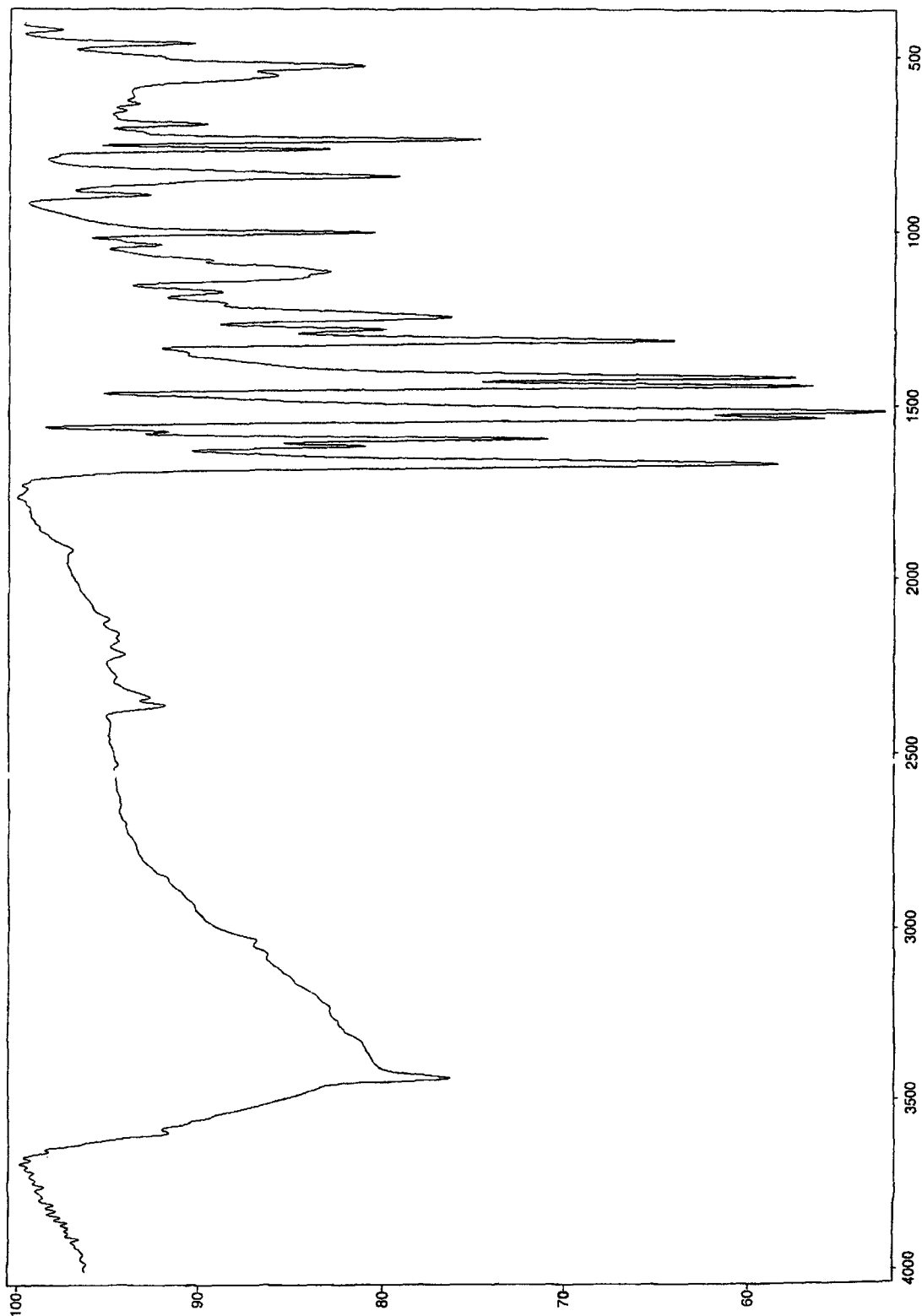
Figure 6b: FT-IR Spectrum of batch B/7081.

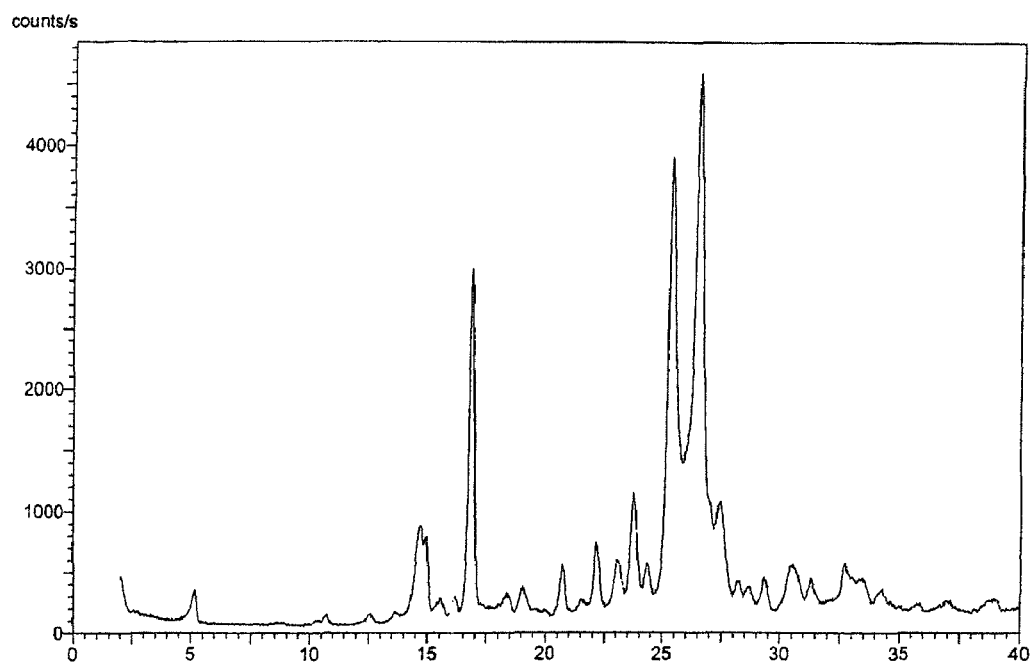
Figure 7a: XRPD Spectrum for unmicronized batch B7081
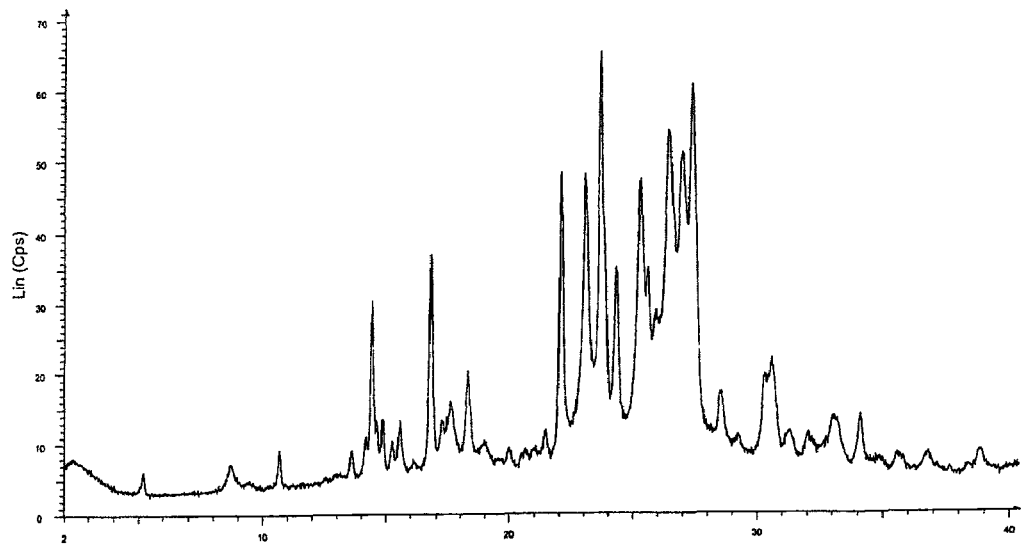
Figure 7b: XRPD Spectrum for micronized batch B/7081

Figure 8: DVS of batch B/6272. left: water content plot vs. relative humidity (the water content was obtained from KF analysis); right: water content vs. time, red line: water content (red scale on the left), blue line represents the R.H. of the chamber vs. time, blu scale on the right.
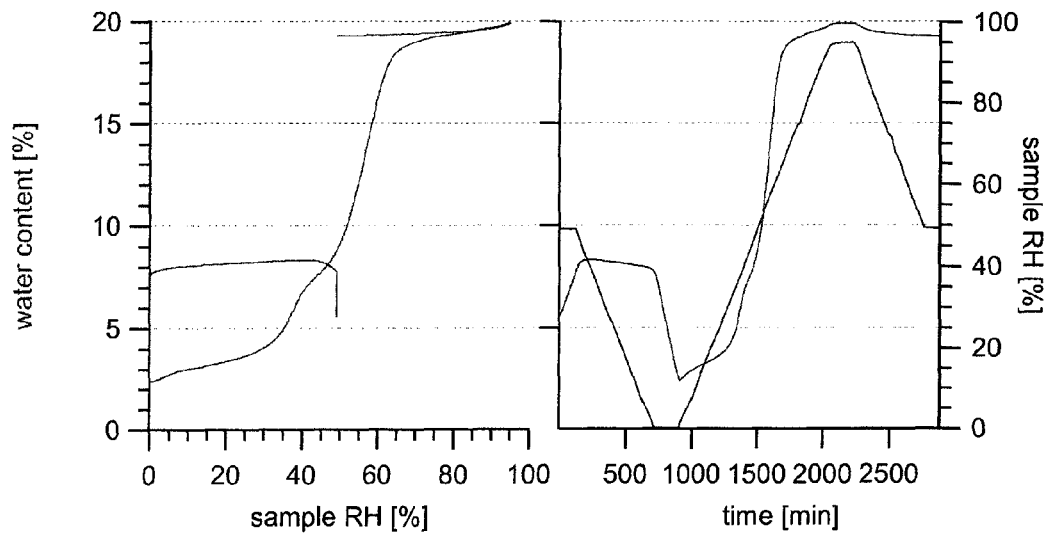
Figure 9a : Fragment 1, view along (a) axis
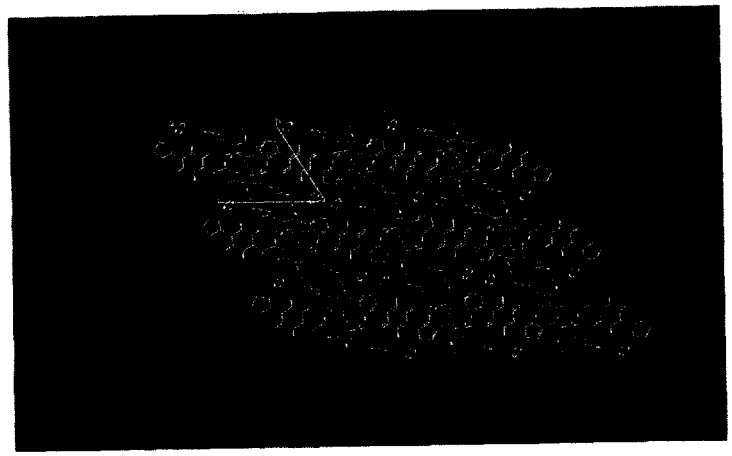

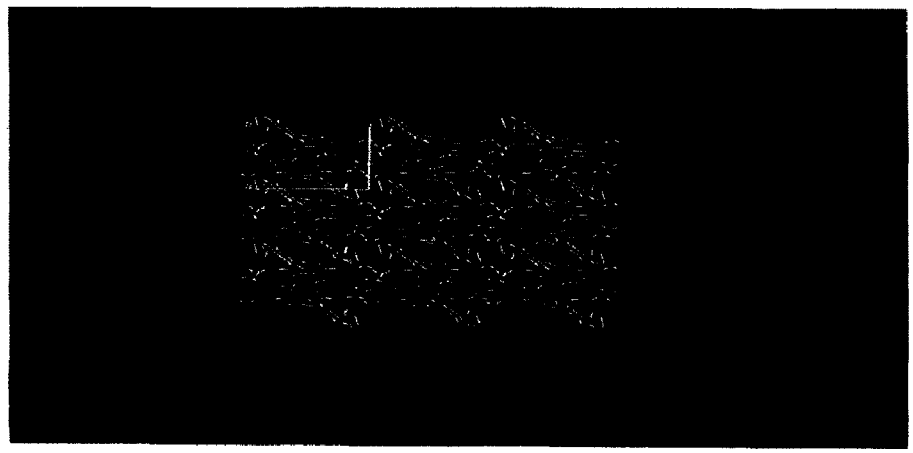
Figure 9b: Fragment 1, view along (b) axis
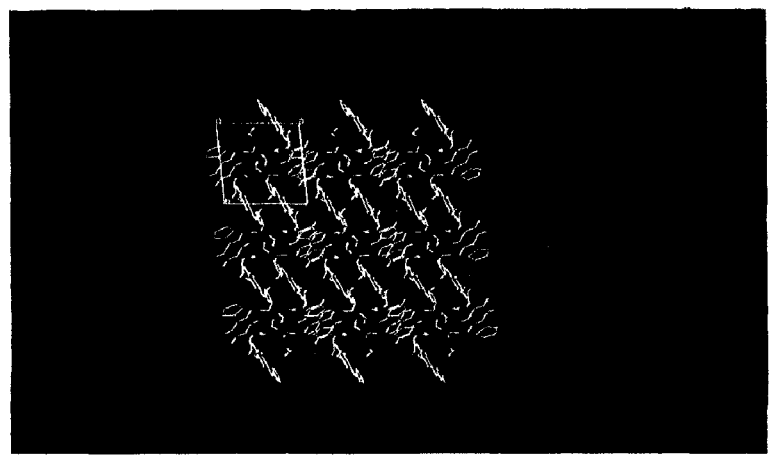
Figure 9c: Fragment 1, view along (c) axis

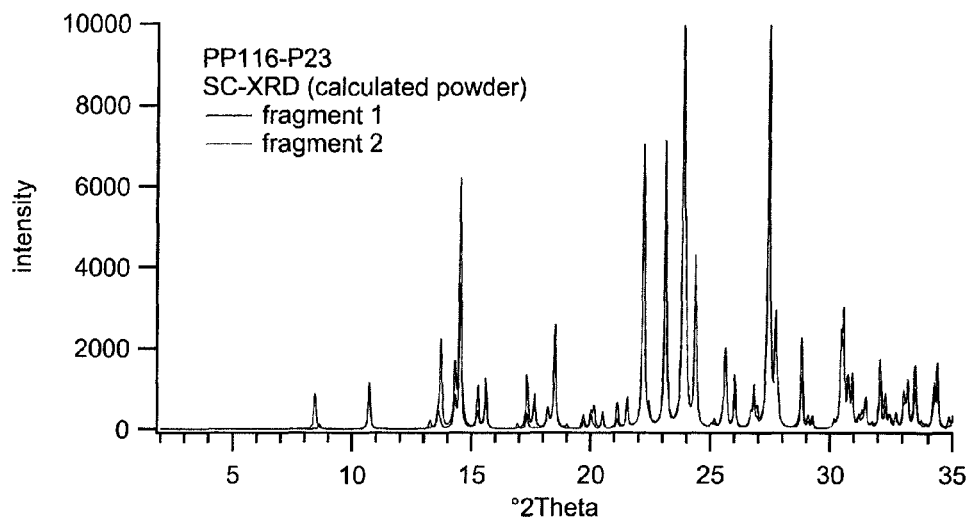
Figure 10: Calculated (theoretical) powder patterns of the two possible orientations (site ocuppancy factor = 1). Some slight differences are visible between the two fragments.
Figure 11a: XRPD spectrum for the product obtained at Example 1.
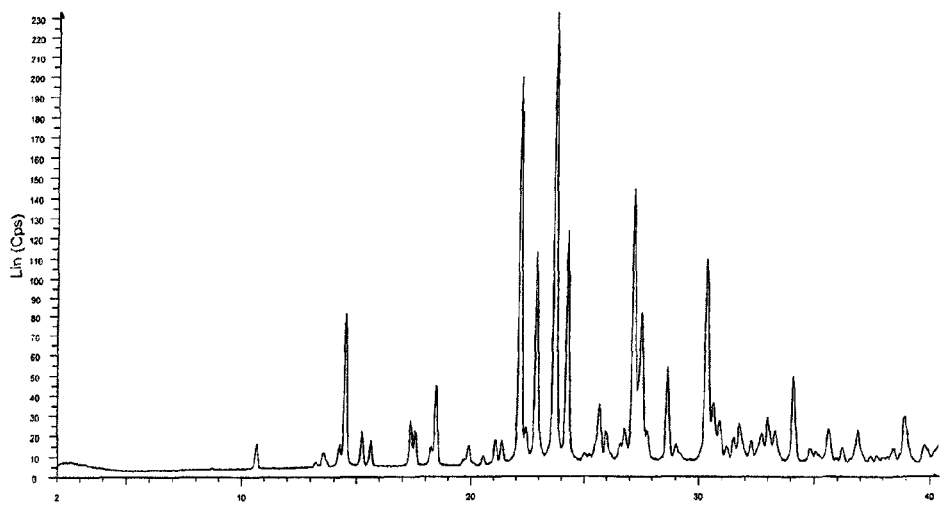

Figure 11b : FT-Raman spectrum for the product obtained at Example 1
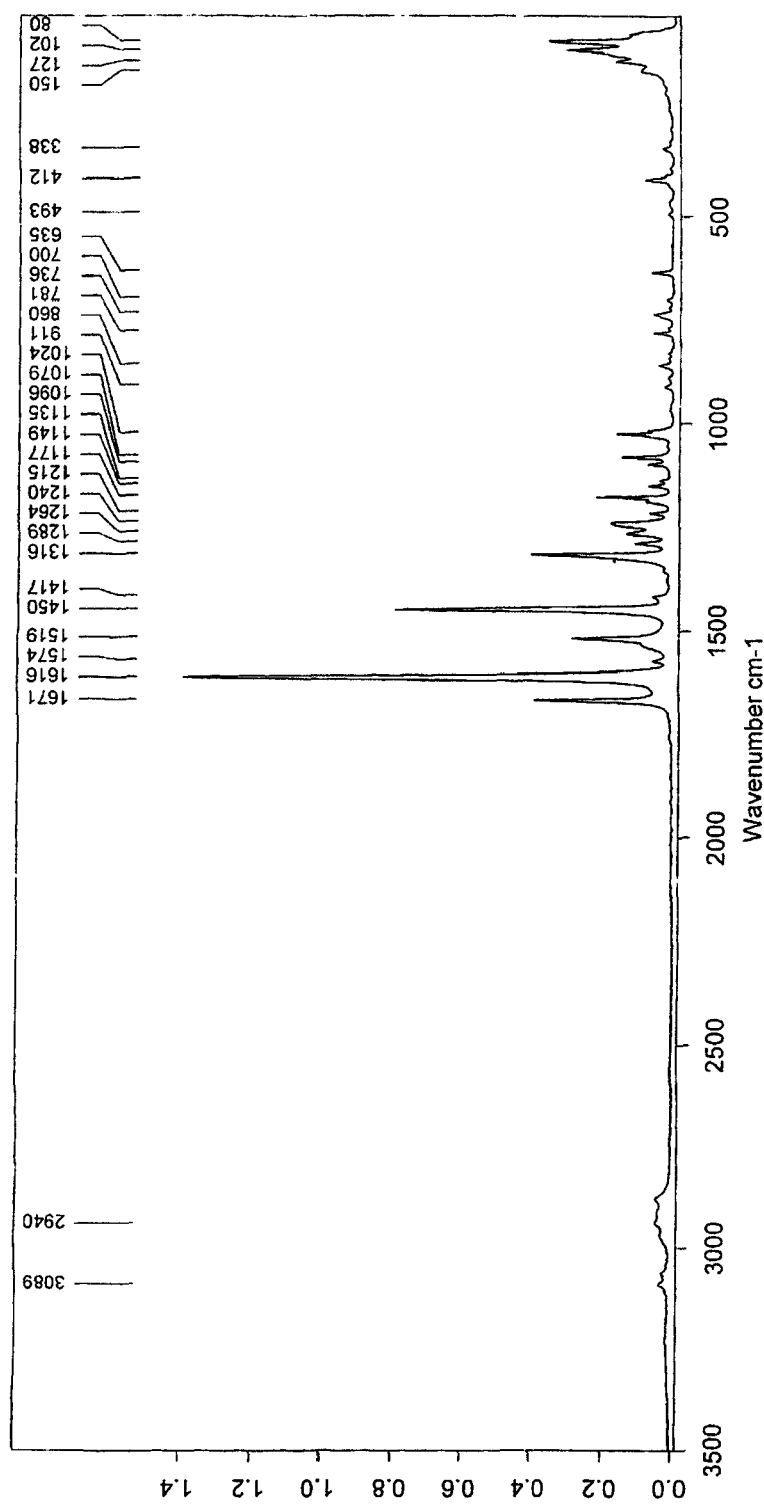

Figure 11c : FT-IR spectrum for the product obtained at Example 1
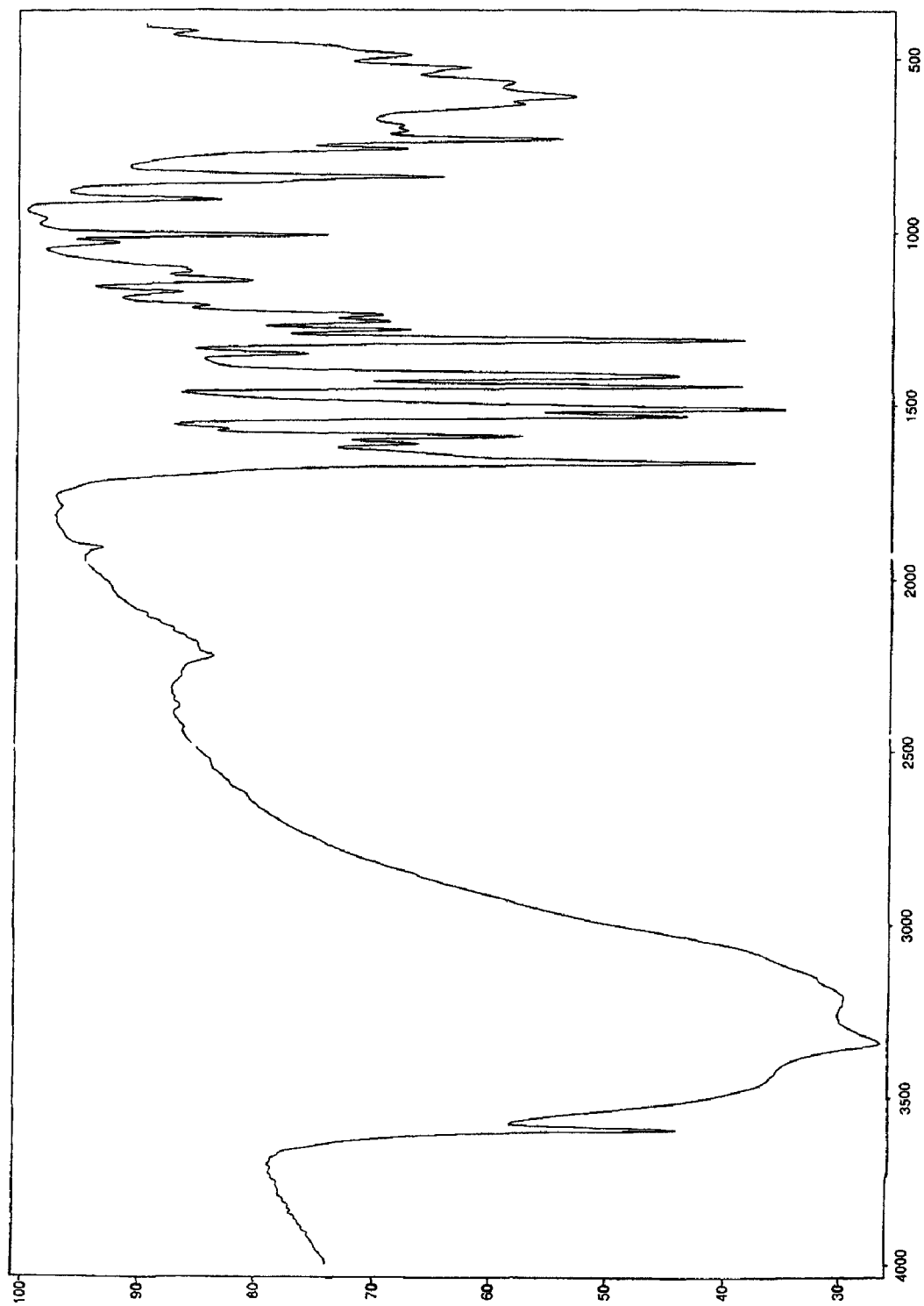

Figure 12a XRPD spectrum for the product obtained at Example 2
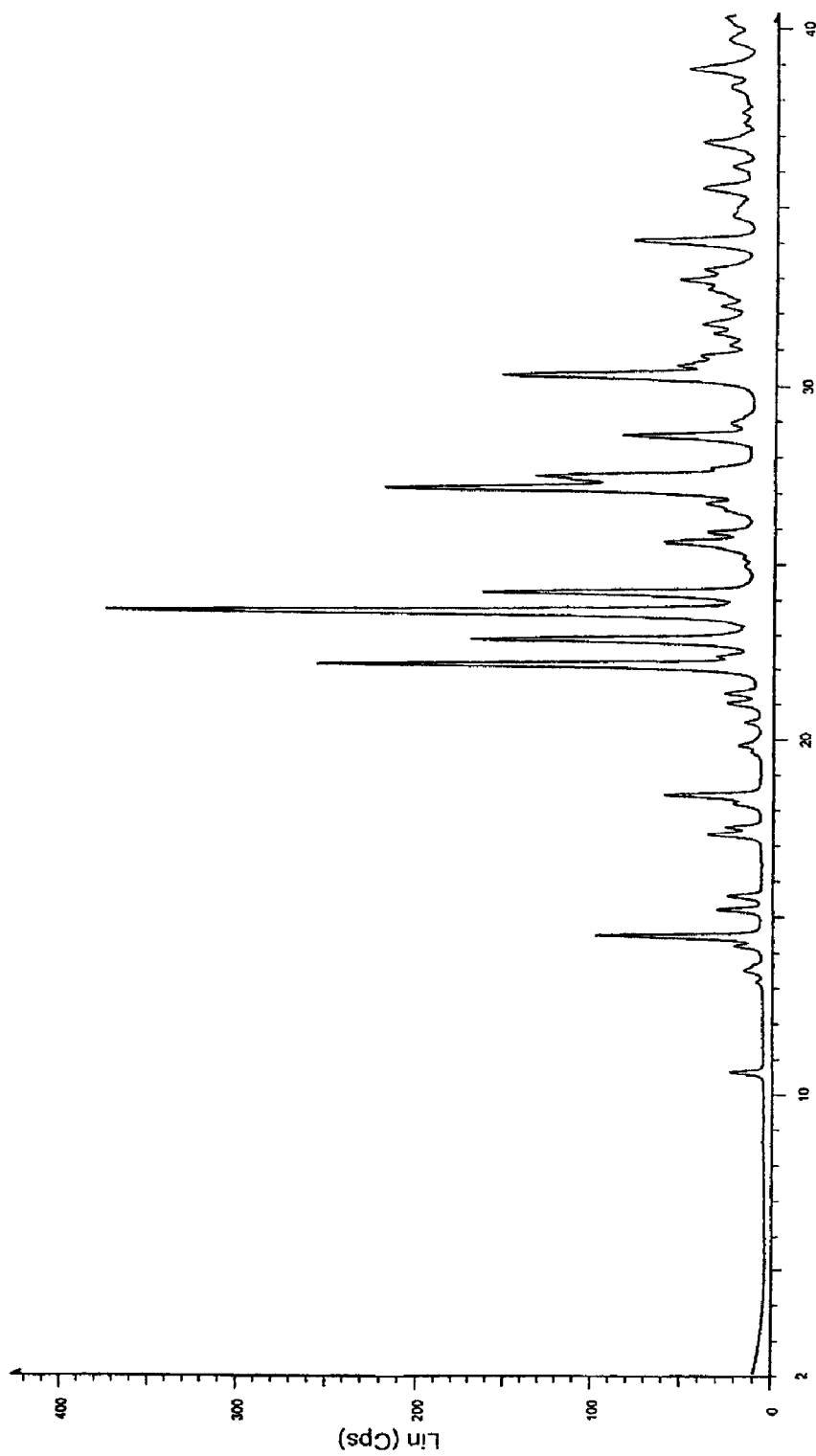

Figure 12b FT-Raman spectrum for the product obtained at Example 2
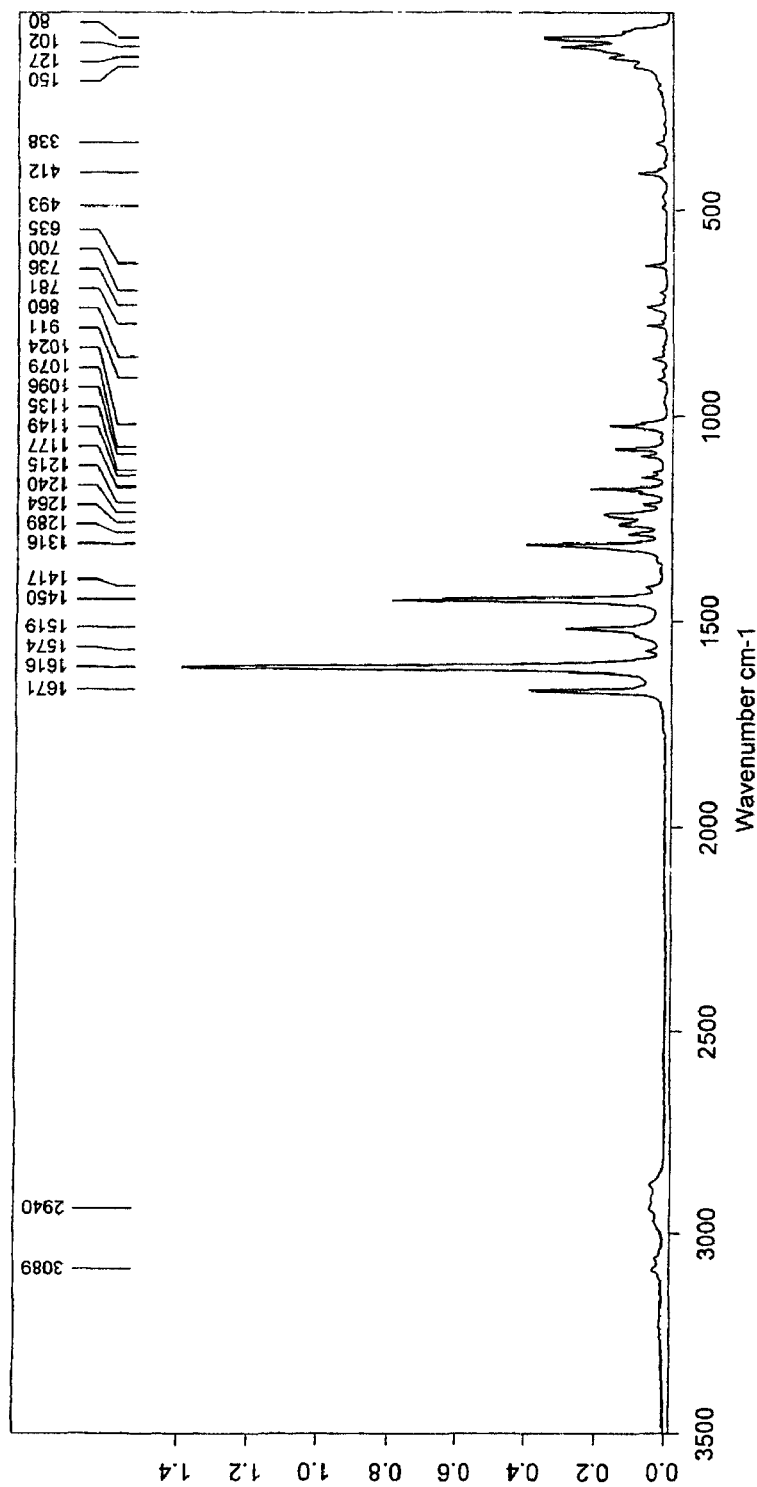

Figure 12c : FT-IR spectrum for the product obtained at Example 2
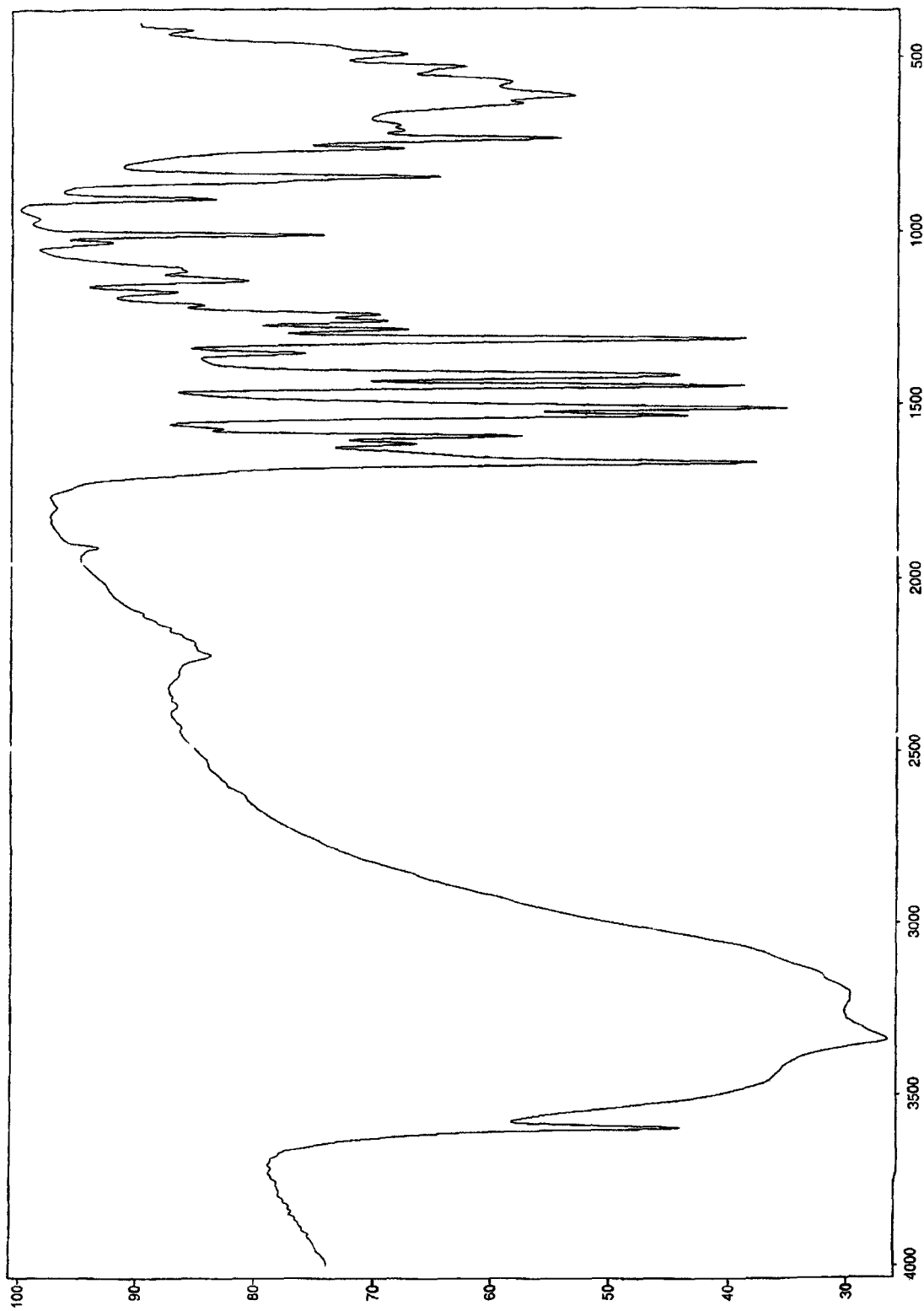

Figure 13a : XRPD spectrum for the product obtained at Example 5
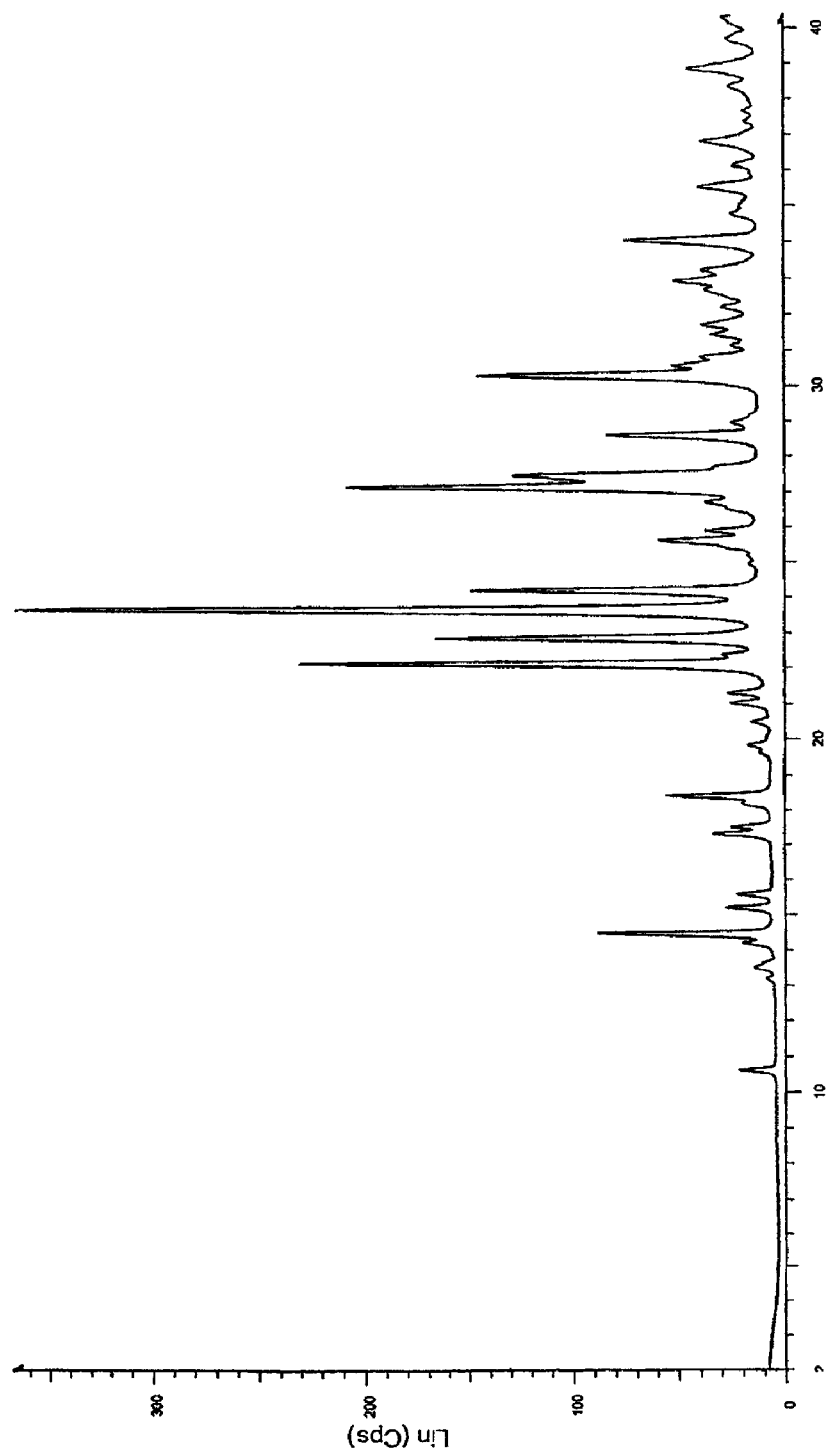

Figure 13b : FT-Raman spectrum for the product obtained at Example 5
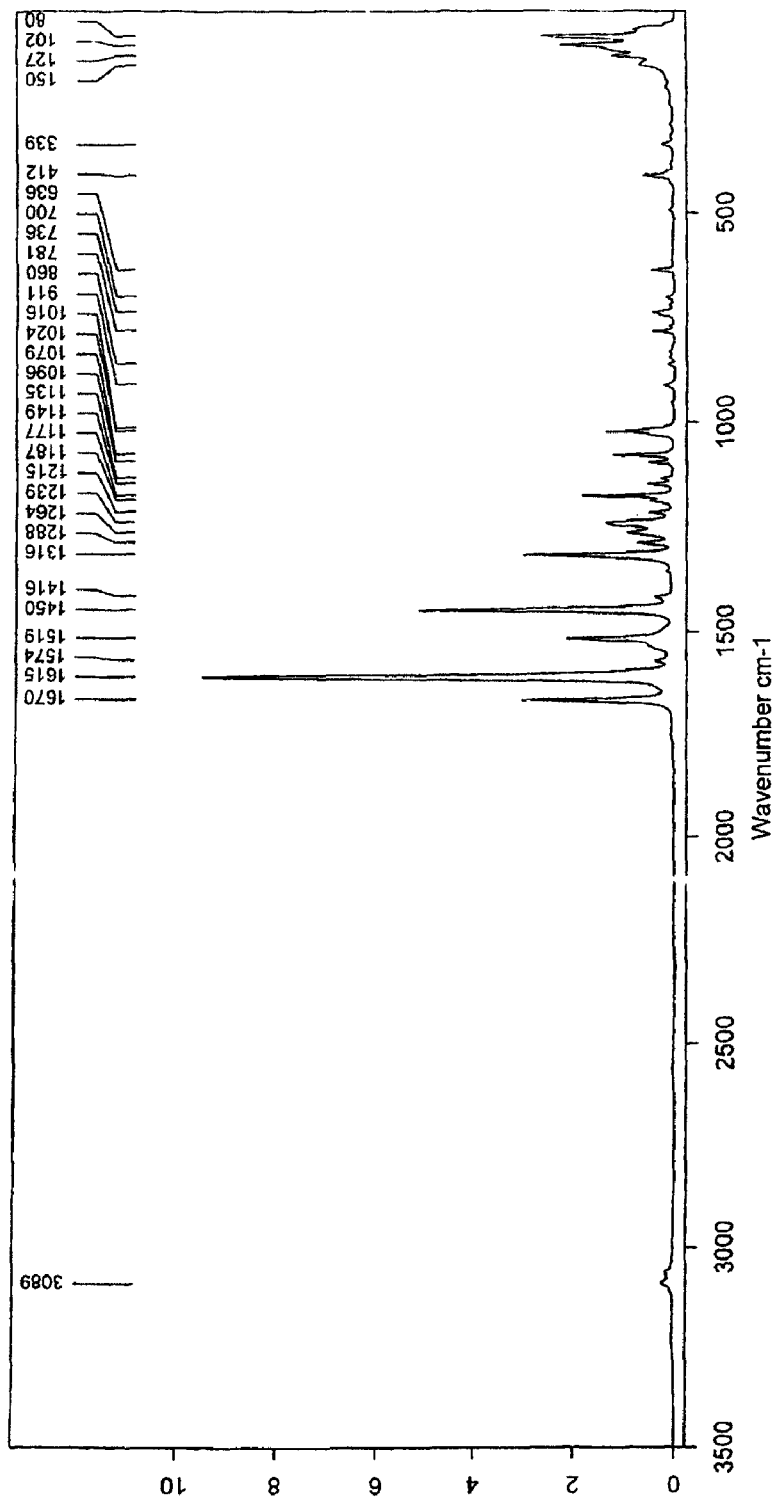

Figure 13c: FT-IR spectrum for the product obtained at Example 5
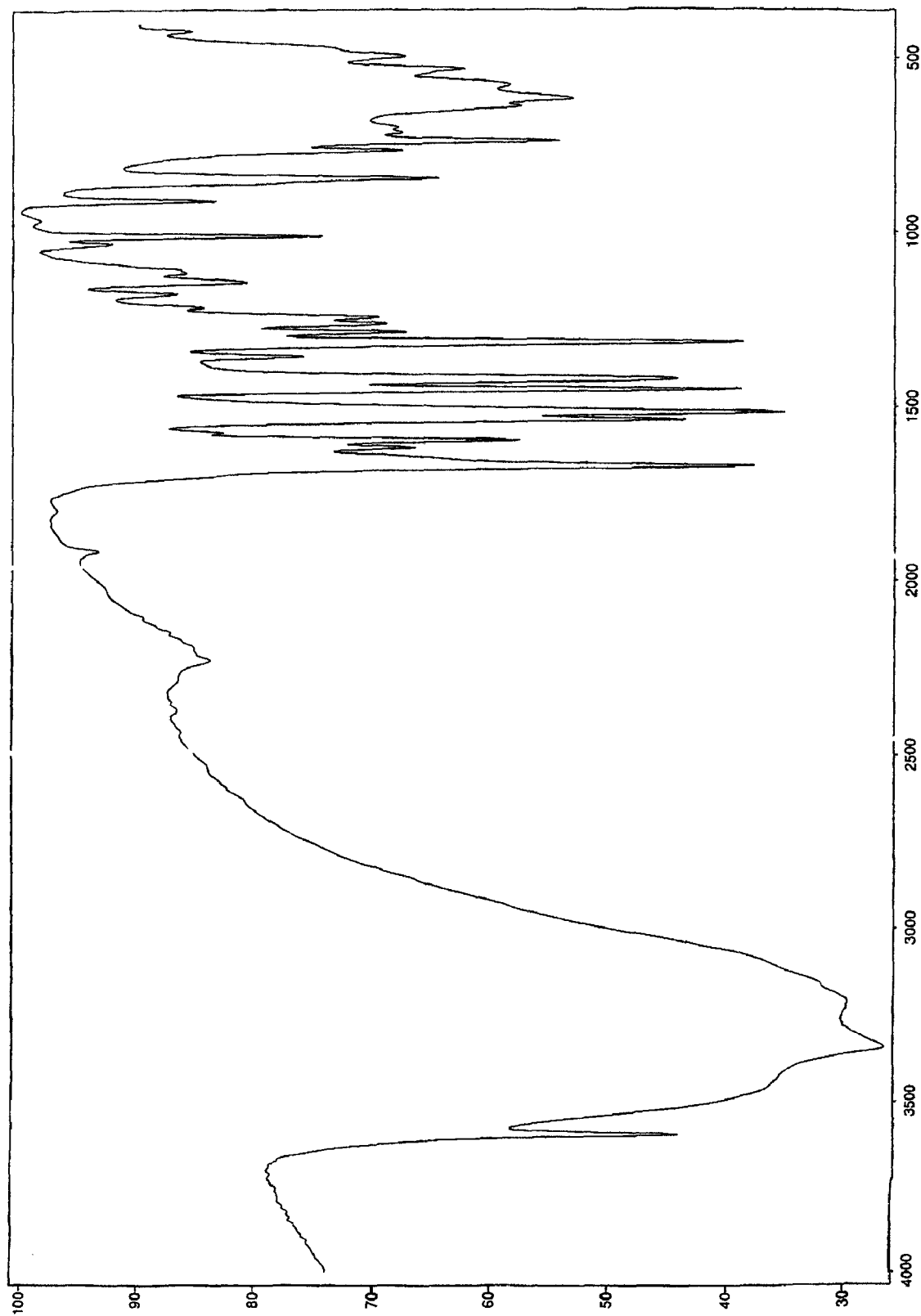

Figure 14: DVS of form A . Water content plot (the water content was obtained from KF analysis).
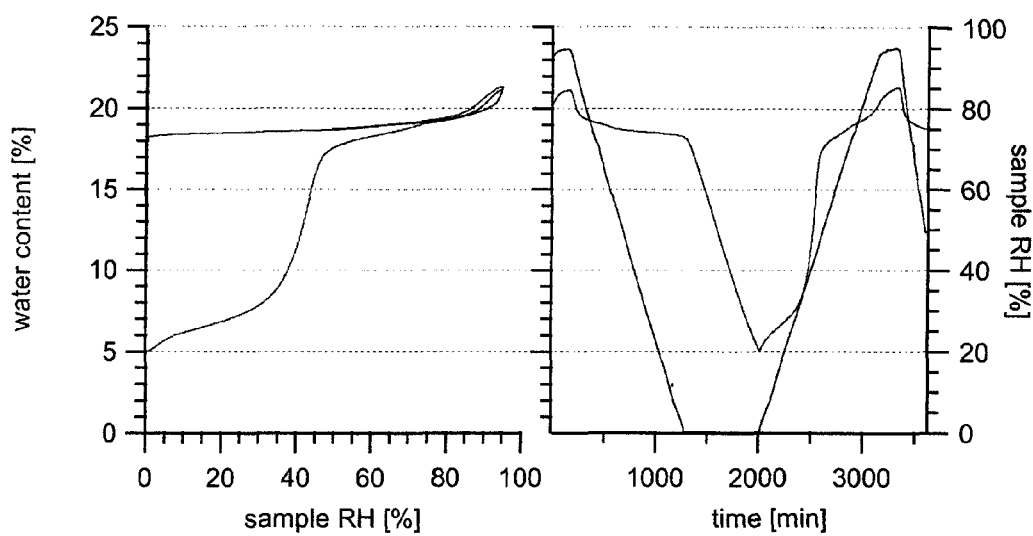

Figure 15a: Form A micronization, XRPD spectrum for Form A micronized material
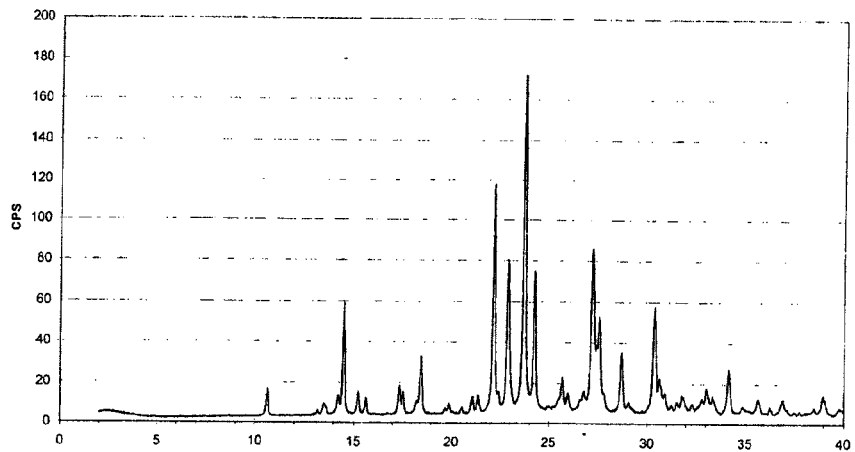
Figure 15b: Form A micronization, FT-Raman spectrum for Form A micronized material
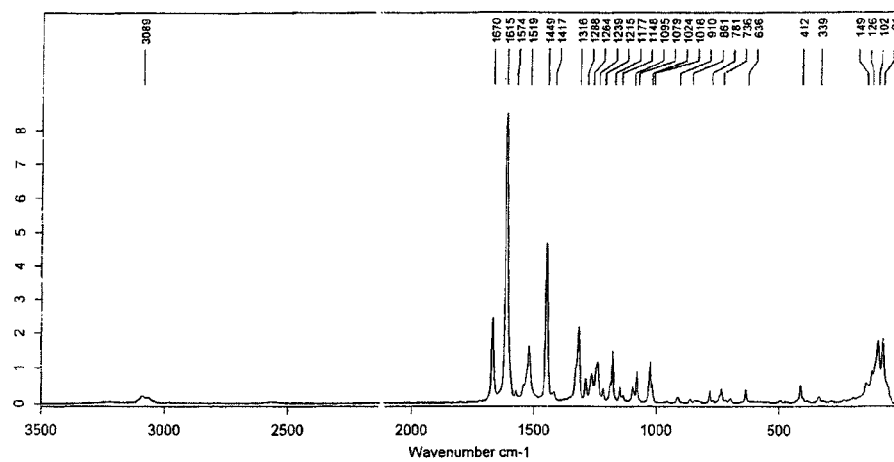

Figure 15c: Form A micronization, FT-Raman spectrum for Form A micronized material
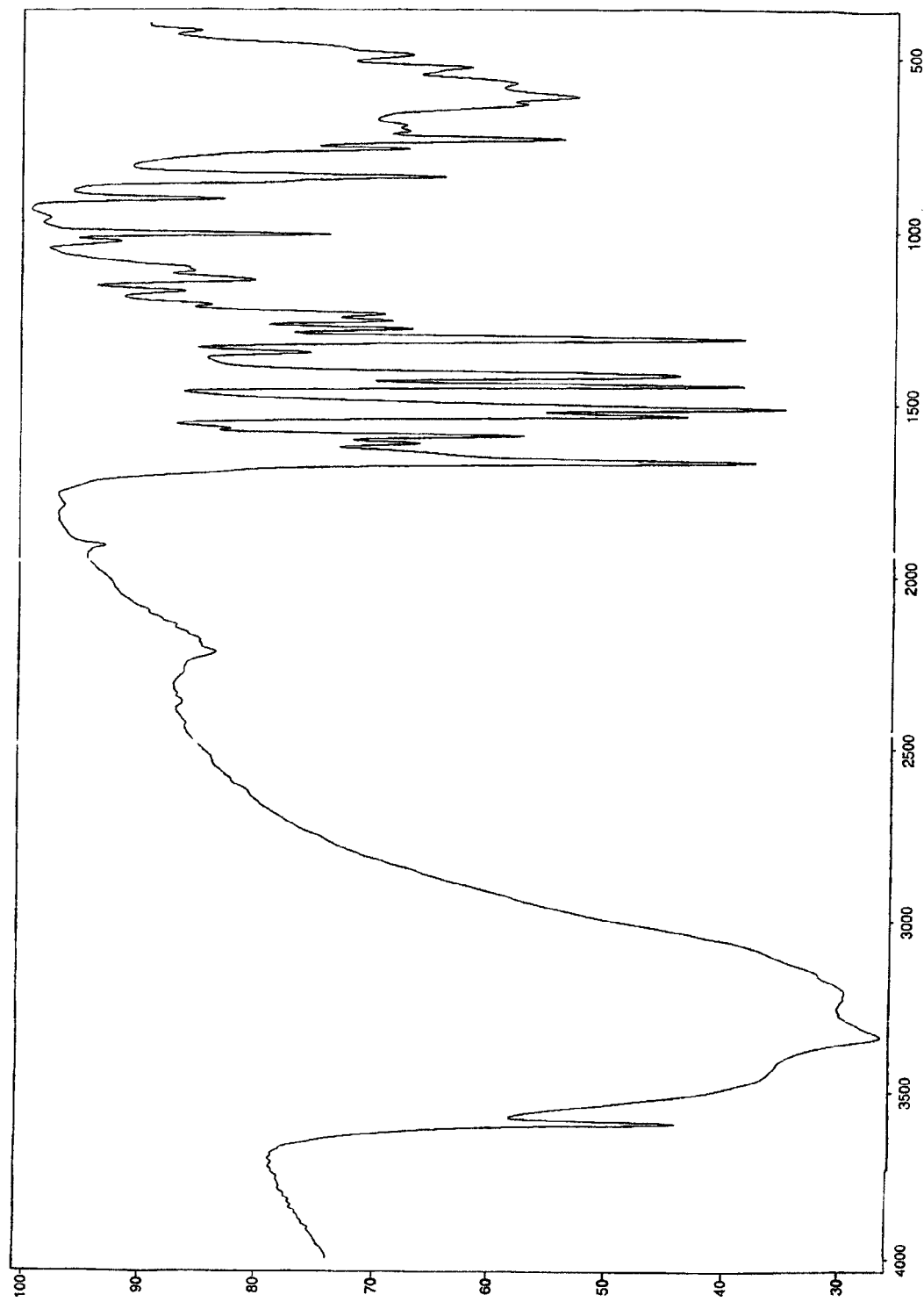

Figure 16: Scanning Electronic Microscopy (SEM) experiments
16 a) Batch B/7080 micronized
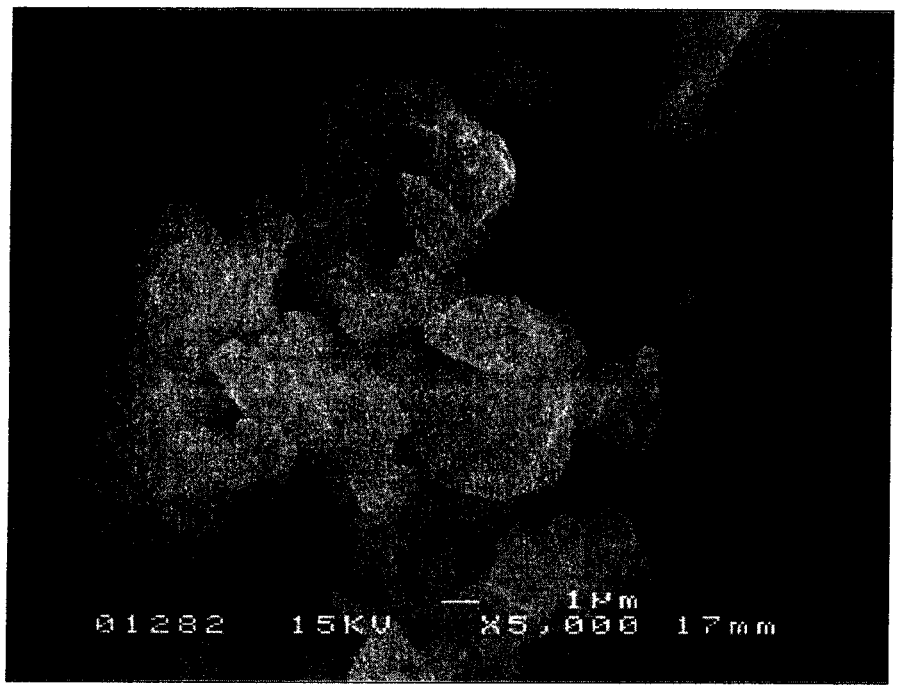
16 b) Micronized Form A
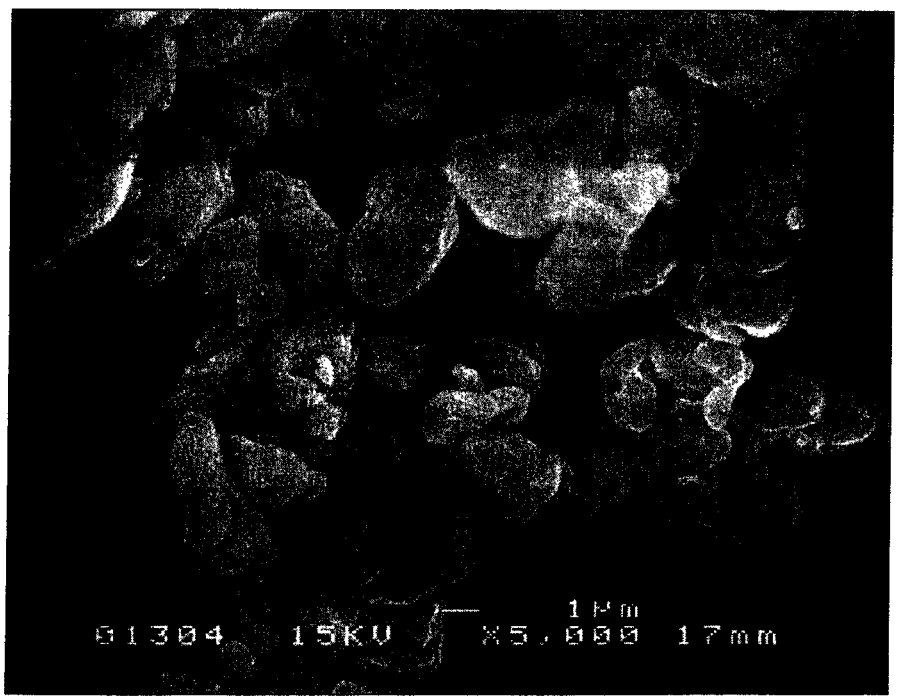

CRYSTALLINE AND STABLE FORM OF ANDOLAST

The present invention relates to physical forms of Andolast, in particular to an hydrate crystalline and highly stable form. The invention further relates to processes for the preparation of such form, to pharmaceutical compositions comprising the compound in such a crystalline form and its therapeutic use thereof.

N-4-(1H-tetrazol-5-yl)phenyl-4-(1H-tetrazol-5-yl)benzamide disodium salt, Andolast disodium salt, CR2039, compound (I):

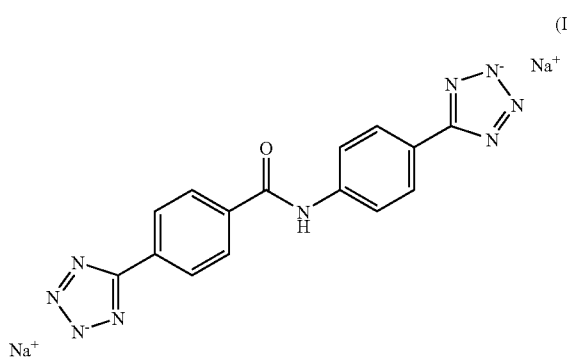

was first described in WO 90/09989, where N-phenylbenzamide derivatives including Andolast and their pharmaceutically acceptable salts are disclosed as therapeutic agents for the treatment of pathological conditions of gastro-intestinal tract and of respiratory system. The anti-allergic and cytoprotective properties of these N-phenylbenzamide derivatives are discussed in J. Med. Chem., 1992, 35, 3633, and the effectiveness of Andolast in the pharmacological treatment of asthma is discussed in European J. Pharmacology, 1992, 229, 45, while its therapeutic relevance for the treatment of COPD is disclosed in EP Application 04019648.

In J. Neural Transmission, 1996, 103 (12), 1371, it was shown how Andolast offers advantages over aminophylline in the treatment of epileptic asthmatic patients, since this drug does not impair the action of conventional antiepileptics (valproate, carbamazepine, diphenylhydantoin) as happens using aminophylline. Parmacokinetics of Andolast disodium salt in mild asthmatic patients after inhalation are discussed in Biopharmaceutics & Drug Disposition, 2001, 22 (2), 73.

Pharmaceutical compositions concerning dry powder for inhalation containing N-4-(1H-tetrazol-5-yl)phenyl-4-(1H-tetrazol-5-yl)benzamide disodium salt, to be used for the treatment of asthma and other pathological diseases of the respiratory tract, are described in EP 896821 and U.S. Pat. No. 5,976,576; in these documents the disodium salt of Andolast, is described as an highly hygroscopic substance which tends to form aggregates easily. When the product is used in the form of a micronized powder, suitable for the treatment of respiratory tract disease by inhalation, the aggregation phenomena can impact negatively upon the performance of the pharmaceutical composition, since it becomes difficult to maintain the particle diameter of the active substance below the 5 µm, limit beyond which it is unlikely the deep penetration of the air passages necessary to the active substance to be absorbed and thus perform its pharmacological activity. In particular to obtain powders where the most of particles are within the range 1.0-3.0 µm is of critical importance in the development of active substances for inhalation (P. J. Atkins, Dry powder inhalers: an overview, Respiratory Care, 2005, 50, 1304), since major determinant of deposition in the respiratory tract is the size and shape of the particles and a good correlation exists between the amount of drug deposited in the lungs and clinical efficacy. Though the problem could be overcome by formulations where an excipient (e.g. lactose) can act as dispersing agent for the active substance, thus leading to de-aggregation by counteracting adhesive forces among particles, this approach is not applicable when rather high dosages of the active substance are required or when interaction properties among particles are particularly strong. In both cases a particularly high amount of the excipients should be used, thus giving rise to an overload of powder to be inhaled by the patient, and consequently to adverse effects such as cough and irritation of the respiratory tract.

More in general, the choice of an appropriate solid form of a drug substance is important when developing a new drug; in view of the fact that most of drug substances exhibit more than one crystalline form it is preferable to develop the more stable one to assure reproducible bioavailability of the product over its shelf life under a variety of storage conditions. Moreover, the crystalline form used in development is significantly based on possible manufacturability, where achievement of process reproducibility avoiding need for special processing conditions and the increasing costs generally associated with such special processing conditions represent key issues (D. Singhal, Drug polymorphism and dosage form design: a practical perspective; Advanced Drug Delivery Reviews, 2004, 56, 335). Finally, regulatory issues require that the form present in a solid dosage form or liquid suspensions be identified from a crystalline form standpoint (ICH Guideline Q6A, 1999; A W Newman, Solid-state analysis of the active pharmaceutical ingredient in drug products, Drug Discovery Today, 2003, 19, 898). In the formulation of drug compositions, it is also important for the drug substance to be in a form in which it can be conveniently handled and processed. Thus the choice of the correct crystalline form is of importance not only from the point of view of obtaining a commercially viable manufacturing process for the active substance but also for the subsequent manufacturing of pharmaceutical formulations comprising the active compound. Crucial physical properties to be taken into account for commercial development are hygroscopicity, kinetic properties such as dissolution rate and stability (including stability at ambient conditions especially to moisture), surface properties such as interfacial tension and shape, mechanical properties such as hardness, tensile strength, mechanical stability, flow and blend properties. Solid state forms that provide an improvement in one or more of these properties relative to other solid state forms are desirable.

SUMMARY OF THE INVENTION

We discovered that, N-4-(1H-tetrazol-5-yl)phenyl-4-(1H-tetra-zol-5yl)benzamide disodium salt, Andolast disodium salt, compound (I), has several stoichiometric and non-stoichio-metric hydrated crystalline forms being the stoichiometric penta-hydrate crystalline form (herein also referred to as: Form A) the most stable one and endowed with suitable physical properties for pharmaceutical formulation and drug product manufacturing.

Accordingly, the present invention is directed to crystalline Form A of Andolast disodium salt, triclinic, displaying a thermal event at 98-112° C. and melting with decomposition at about 400° C. (DSC), characterized as reported in Table 1 and FIG. 1, by the X-ray powder diffraction (XRPD) pattern expressed in terms of the 2θ, d-value and relative intensity, when obtained from a copper radiation source:

TABLE 1

XRPD Spectrum for Form A (intensity ≧ 10%)

| Angle 2-theta | d-value (Å) | Intensity % |
|---|---|---|
| 14.45 | 6.10 | 23 |
| 18.39 | 4.82 | 14 |
| 22.10 | 4.02 | 64 |
| 22.82 | 3.89 | 45 |
| 23.63 | 3.76 | 100 |
| 24.17 | 3.68 | 41 |
| 25.60 | 3.48 | 15 |
| 25.90 | 3.44 | 10 |
| 26.71 | 3.34 | 10 |
| 27.10 | 3.29 | 58 |
| 27.42 | 3.25 | 31 |
| 28.59 | 3.12 | 22 |
| 30.28 | 2.95 | 39 |
| 30.56 | 2.92 | 14 |
| 30.83 | 2.90 | 10 |
| 31.72 | 2.82 | 10 |
| 32.94 | 2.72 | 13 |
| 33.25 | 2.69 | 10 |
| 34.06 | 2.63 | 21 |
| 35.56 | 2.52 | 11 |
| 36.82 | 2.44 | 10 |
| 38.88 | 2.31 | 12 |

Further, the second aspect of the present invention is directed to crystalline Form A of Andolast disodium salt, characterized by the FT-IR spectrum as reported in FIG. 2. FT-IR spectra herein reported are measured using an ATI Mattson Genesis Instrument, 1% (w/w) dispersion in KBr disk.

In a third aspect, the present invention is directed to crystalline talline Form A of Andolast disodium salt, characterized by the FT-Raman spectrum as reported in FIG. 3. FT-Raman spectra herein reported are measured using a Bruker RFS100 instrument, YAG 1064 nm excitation, 100 mW laser power, Ge-detector, 64 scans, range 25-3500 cm$^{-1}$, 2 cm$^{-1}$ resolution.

In a further embodiment, this invention provides processes for preparing crystalline Form A of Andolast disodium salt.

In a still further embodiment, this invention provides pharmaceutical compositions comprising the crystalline Form A of Andolast disodium salt.

DETAILED DESCRIPTION OF THE INVENTION

N-4-(1H-tetrazol-5-yl)phenyl-4-(1H-tetrazol-5-yl)benzamide was prepared according to the process described in WO90/09989, and the corresponding disodium salt was precipitated according to conventional methods (J. Med. Chem., 1992, 35, 3633), which mainly consisted in the addition of a sodium hydroxide aqueous solution to the product in its acid form, dissolved in a water-miscible organic solvent.

The disodium salt obtained according to this process was highly hygroscopic independently upon the organic solvent used for the precipitation; re-crystallization of the product, though improved its chemical purity, did not improve its chemical-physical characteristics, and also by re-crystallization an hygroscopic material difficult to be transformed in pharmaceutical formulation was always obtained from several solvents, according to conventional crystallization procedures. Not only the highly hygroscopic characteristics of the drug substance impacted its manufacturing process and storage conditions (in particular for stability to moisture), but also hampered the manufacturing of the dosage form due to unfavorable mechanical properties which affected flow and blend properties. In addition those formulation involving Andolast disodium as dry powder for inhalation, due to particles interfacial tension, displayed a poor performance in terms of delivered dose and fine particle fraction, particularly when formulations characterized by a low dilution of the drug substance in the excipients were used. Pharmaceutical manufacturing process development highlighted a remarkable batch-to-batch variability in the physical characteristics of the drug substance, apparently related to the water content (assessed by the Karl-Fisher method). A more in depth investigation carried out on the drug substance highlighted how this batch-to-batch variability could be also related to some differences in the XRPD and FT-Raman spectra of the product, obtained according to apparently quite similar conditions, that corresponded to the precipitation of Andolast disodium salt as above described, and drying (in FIG. 4a-d, XRPD spectra of four batches manufactured according to conventional procedures are reported; in FIG. 5a-d, FT-Raman spectra of the same four batches are reported).

It is well known in the crystallography art that, for any given crystalline form, the relative intensities of the diffraction peaks may vary due to preferred orientation resulting from factors such as crystal morphology. Where the effects of preferred orientation are present, peak intensities are altered but the characteristic peak positions of the same crystalline form are unchanged (see e.g., USP issue 23, National Formulary 18, pages 1843-1844, 1995). This peak position consistency is not recognizable comparing spectra in FIG. 4a-d, looking at the spectra of the several batches though some pattern are similar different peaks are present, suggesting that they are dealing with more than one crystalline line structure. This conclusion can be confirmed comparing FT-Raman spectra for the same lots in FIG. 5a-d.

Conversely, no significant differences are observed in the FT-IR spectra of these batches as appears by comparing the FT-IR spectra of two representative batches (B/7080 and B/7081) reported in FIG. 6a-b.

In addition, for those formulations where Andolast disodium salt is used as powder for inhalation, a micronization step is necessary in order to provide the drug substance in the proper particle size distribution (PSD), which is critical for an appropriate absorption by the respiratory tract as above discussed. This additional operation resulted in a further source of variability for Andolast disodium salt, since a striking change in the XRPD pattern as well as in FT-Raman spectra appeared after the micronization step of the lots above described, suggesting that further changes or adjustments in the crystalline habits of these materials occurred during micronization.

In FIGS. 7a and 7b XRPD spectra for-batch B/7081, respectively unmicronized and micronized, are reported as an example.

The different above described batches, also displayed differences in hygroscopicity studies. The moisture sorption/desorption behavior was analyzed for different solids using Differential Vapor Sorption (DVS) technique. In FIG. 8 is reported as an example the sorption/desorption isotherms for batch B/6272. Storing of the sample at 50% R.H. (R.H.: Relative Humidity) at the beginning of the measurement results in immediate sorption of water, indicating the strongly hygroscopic character of the solid. The solid showed a continuous sorption of moisture reaching a plateau at about 20% of water content. Though the different batches were not characterized by exactly matching DVS diagrams all reached the about 20% water content after an appropriate time.

These striking variations in drug substance physical characteristics strongly pointed out needs for further development of a stable, not hygroscopic, well characterized and reproducible crystalline form of Andolast disodium salt.

We discovered that though Andolast disodium salt has several hydrated forms both stoichiometric and non-stoichiometric, that can account for the observed variations in physical characteristics, different hydrated forms can be obtained according to the manufacturing process conditions. We also discovered that the pentahydrate, herein named Form A, is surprisingly the most stable one under a very large range of real-world conditions, not hygroscopic, endowed with unexpected good physical properties such as surface properties (interfacial tension and shape), mechanical properties such as compressibility, hardness and strength, as well as good flow and blending properties which make it suitable for the handling in the preparation of pharmaceutical formulations, and particularly in obtaining drug products suitable for inhalation. The Form A can be obtained with high reproducibility and consistency when crystallized and dried according to well defined and controlled conditions. The Form A, among the several hydrated forms, is the one with the higher degree of crystalline structure, wherein the molecules are arranged to form a distinguishable crystal lattice comprising a defined unit cell and yielding regular and reproducible diffraction peaks when subjected to X-ray radiation. All other hydrates forms, whose crystalline structure can be considered as a distortion of the pentahydrate crystalline structure, are less ordered and hence endowed with lower stability and less favorable physical characteristics.

A careful study of the crystallization conditions of Andolast disodium salt, highlighted how the water activity (i.e.: polarity and hydrogen bond characteristics of the crystallization solvent along with the amount of water present within the crystallization medium) can impact the hydration degree of the obtained product. In addition, also the procedures used for isolation (for example: washings) and drying can significantly influence the type of the resulting hydrate.

The final crystallization in the manufacturing process consists of precipitating the desired salt out of an aqueous solution by addition of an anti-solvent. As intended herein an "anti solvent" is a water miscible organic solvent which dramatically reduces product solubility in water. It is to point out that the water activity in such environments is different for the different solvents. Based on water miscibility and solubility for the different solvents, solid to solvent ratio, water content of the crystallization medium, different solids with different water content can be obtained.

Phase equilibration experiments demonstrated how the different solids obtained could be inter-converted one to each other, or converted into new products with different physical characteristics depending upon the solvent, the amount of water present, the time and temperature.

For "phase equilibration experiment" herein is intended a process in which a slurry of Andolast disodium salt is stirred in a solvent or mixture of solvents for a certain time and at a defined temperature.

As limit examples of how the crystallization medium can impact the obtained hydrated form the following phase equilibration experiments are reported:

about 100 mg of lot B/3610 (KF: 10.74%) were stirred at r.t. for 24 hours in 0.3 mL of isopropanol. The solid was isolated and dried for 10 min. under vacuum. The KF of the obtained product was 8.5%; the XRPD and FT-Raman spectra of this product differed from the one of the starting material;

about 100 mg of lot B/3610 (KF: 10.74%) were stirred at r.t. for 24 hours in 0.3 mL of acetone. The solid was isolated and dried for 10 min. under vacuum. The KF of the obtained product was 2.3%; the XRPD and the FT-Raman spectrum of this product differed from the one of the starting material);

about 100 mg of lot B/3610 (KF: 10.74%) were stirred at r.t. for 24 hours in 0.3 mL of 1-1 isopropanol-water mixture. The solid was isolated and dried for 10 min. under vacuum. The KF of the obtained product was 20.1%; the XRPD and the FT-Raman spectrum of this product differed from the one of the starting material;

about 100 mg of lot B/3610 (KF: 10.74%) were stirred at r.t. for 24 hours in 0.3 mL of 1-1 acetone-water mixture. The solid was isolated and dried for 10 min. under vacuum. The KF of the obtained product was 19.6%, the XRPD and the FT-Raman spectrum of this product differed from the one of the starting material.

For comparison, lots B/6272 (KF: 5.35%), B/3610 (KF: 10.74%), B/6981 (KF: 1.08%) and B/7081 (KF:5.53%) were obtained respectively: B/6272 by crystallization from an acetone-water mixture (about 6:1), then dried overnight at 90° C., B/3610 was obtained by crystallization from a not measured acetone-water mixture, then dried overnight at 110° C., B/6981 was obtained by crystallization from n-propanol after azeotropic distillation of most of the water, then dried at constant weight at about 50° C., and B/7081 was precipitated from an isopropanol-water mixture of about 10:1, then dried at constant weight at about 90° C.

Drying procedures can also affect the obtained product as appears by the following experiment:

about 100 mg of lot B/3610 (KF: 10.74%) were dried until rotary oil pump for 24 hours; KF of the obtained product was 3.2%; the XRPD and the FT-Raman spectrum of this product differed from the one of the starting material.

In Table 4 is reported the theoretical water content for different stages of hydration for Andolast disodium salt.

TABLE 4

| | Molecules of water | | | | | |
|---|---|---|---|---|---|---|
| | 1 | 2 | 3 | 4 | 5 | 6 |
| Theoretical water content (%) | 4.6 | 8.7 | 12.5 | 16.0 | 19.3 | 22.3 |

Considering that the batches obtained according to conventional crystallization and drying procedures (some of them have been reported as example, i.e.: batch B/6272, KF: 5.35%; B/3610, KF: 10.74%; batch B/6981, KF: 1.08%; B/7081, KF: 5.53%), did not match the Karl-Fisher test for the water content for any of the values reported in Table 4, along with the continuous trend in water sorption/desorption in DVS experiments (up to about 20% R.H.), it could be speculated that for these materials, even though ready transformation of hydrated forms one into the other was possible, some additional water absorption mechanism, able to incorporate water molecules into the lattice leading to a non-stoichiometric hydrate, was possible as well. The observed changes in the XRPD and FT-Raman patterns indicated that the unit cell dimensions were changing when changing the water content, presumably both to accommodate molecules into the crystal structure and weakly held water molecules as the relative humidity is increased.

Moreover, the stabilization in water content noticed at about 20% in the DVS experiments, common to all the materials tested suggested that a stable hydrated form should be present at about 20% of water, corresponding to the hexahydrate or to the pentahydrate looking at values in Table 4.

Single Crystal XRD (SC-XRD)

Very slow crystallization experiments using conditions characterized by high water activity were carried out. A stock solution obtained by dissolving about 500 mg of Andolast disodium salt in 10 mL of water was prepared. In one experiment to 2 mL of the stock solution were added 18 mL of acetone. In a second experiment 18 mL of isopropanol were added to the stock solution (2 mL). Both the obtained solutions were stirred at r.t. for three days. While no precipitation occurred from the acetone-water solution the isopropanol-water solution led to the formation of a crystal of about 1 mm size suitable for SC-XRD and other chemical physical assessments. Stirring of a portion of this crystal at r.t. for a further month in a 1:9 isopropanol-water saturated solution did not change the physical characteristics (DVS, XRPD, FT-Raman) of the product, confirming this form is stable in these conditions.

The crystal was measured on a Nonius Kappa CCD diffractometer at 173K, using graphite-monochromated Mo $K_\alpha$—radiation with $\lambda$=0.71073 Å, $\theta_{max}$=27.915°. The COLLECT suite has been used for data collection and integration. From a total of 9305 reflections, 4704 were independent (merging r=0.012). From these, 3531 were considered as observed (I>2.00$\sigma$ (I)) and were used to refine 335 parameters. The structure was solved by direct methods using the program SIR92. Least-squares refinement against F was carried out on all non-hydrogen atoms using the program CRYSTALS. R=0.0340 (observed data), R=0.0562 (all data), GOF=0.8974. Minimal/maximal residual electron density 0-0.24/0.27 e Å$^{-3}$. Sheldrick weights were used to complete the refinement. The central part of the molecule is disordered and has been refined using appropriate restraints. The disorder is set up in a way that does not have any impact on the hydrogen bonding scheme present in the structure. Hydrogen atoms have been located in the difference map, but refinement has been done with hydrogens in calculated positions or, in the case of water molecules, with the located positions linked to the position of corresponding oxygen atom.

The single crystal above obtained was analyzed as described, the following crystal data were found:

Formula: $C_{15}H_{19}N_9Na_2O_6$, MW: 467.35, colourless plate, size 0.17*0,19*0.26 mm$^3$, triclinic space group P-1, Z=2, a=8.2787(1) Å, b=11.4162(2) Å, c=11.6498(1) Å, $\alpha$=63.9390(7)°, $\beta$=88.2585(7)°, $\gamma$=85.3018 (7)°, V=985.75 (2) Å$^3$, $D_{calc}$: 1.574 mg mm$^{-3}$.

The solid consisted of a penta-hydrate with crystal defects; about 20% of the single molecules arrange miss-oriented (i.e. they are rotated of 180° in comparison to the rest of the molecules; see FIG. 9a-c). This is due to Andolast pseudo-symmetry, where the two identical branches of the molecules constitute an element of high symmetry disturbed by the presence of a non-symmetric amide group in the centre of the molecule. It is well conceivable that depending on the crystallization conditions (i.e. solvent, speed, temperature) more or less molecules are miss-oriented. Since the missorientation results in a slight distortion of the molecule and to a very small cell dimension change, these effects could also be detected in the XRD pattern. FIG. 10 shows the theoretical, calculated powder patterns of crystals having either all molecules in one or the other orientation (the two possible different orientation are named fragment 1 and fragment 2). Comparing the two patterns in FIG. 10, only slight differences are recognizable between the two fragments.

The view along the three crystallographic axis (see FIG. 9) reveals the particular arrangement of the Andolast disodium salt penta-hydrate (Form A) molecules. Channel like structures in all three dimensions are visible. It could be speculated that in addition to the five molecules of crystallization water further water molecules (coordinated water) could be located in these channels, this could explain the continuous water sorption behaviour previously discussed.

Molecular mechanics simulation carried out on this pentahydrate structure showed that upon removing water crystallization molecules a certain degree of distortion is introduced within the crystal structure, being this distortion proportional to the number of the water molecules removed.

Accordingly, lower hydrates (for example: mono-hydrate and di-hydrate) are expected to be remarkably less stable in comparison to higher hydrates (for example: tri-hydrate and tetra-hydrate), this should account for the dramatic hygroscopicity found for the de-hydrated materials above described. According to this model all lower hydrates (from 4 to 1 water molecules) structures can be obtained by removing water molecules from the supra-molecular structure reported in FIG. 9 which is then distorted in order to maintain as higher as possible the hydration around the charged part of the molecule. This model strongly supports a lower stability and worst mechanical properties for lower hydrates in comparison to the penta-hydrate.

Preparation of Andolast Disodium Penta-Hydrate (Form A)

N-4-(1H-tetrazol-5-yl)phenyl-4-(1H-tetrazol-5-yl)benzamide is prepared as described in WO 90/09989, Example 13 (herein incorporated by reference). The disodium salt of N-4-(1H-tetrazol-5-yl)phenyl-4-(1H-tetrazol-5-yl)benzamide can be prepared directly as the pentahydrate or precipitated as an undefined mixture of hydrates and then converted into the pentahydrate (Form A), by re-crystallization or by phase equilibration (slurry conversion: slurry in an appropriate solvent mixture). In both cases the disodium salt is obtained by adding to a suspension in water of N-4-(1H-tetrazol-5-yl) phenyl-4-(1H-tetrazol-5-yl)benzamide, an amount of aqueous sodium hydroxide or sodium alkoxide, ranging from 2.0 to 2.2 equivalents, preferably 2.1 equivalents, being sodium methoxide, sodium ethoxide and sodium isopropoxide the preferred alkoxide, at a temperature ranging from +15° to +40° C. The preferred volume of water to be used for preparing the salt is depending on the operating temperature, solubility of the disodium salt in water is about 150 g/L at 25° C. The resulting mixture is stirred until the solid is completely dissolved, then the pH of the solution is carefully adjusted to 6.5-7.5, by addition of diluted hydrochloric acid, filtered and concentrated under vacuum, at a temperature not exceeding +60° C. The final volume of this concentration will depend on the procedure is used for obtaining the Form A. For those cases where the Form A is obtained by re-crystallization or phase equilibration of a mixture of hydrates, the concentration will be carried out until a dense oil is obtained. Then an appropriate water-miscible solvent is added under stirring, at a temperature ranging from +5° C. to +60° C., and the product is crystallized or by cooling or simply by stirring the obtained mixture at the appropriate crystallization temperature. Crystallization temperature being dependent on the type of the solvent used, on the water-solvent ratio, and on the concentration of the product in the crystallization mixture. Alternatively, the solution of the disodium salt in water, described above, can be taken up with an appropriate solvent which forms an azeotropic mixture with water. Replacement distillation (that is distilling the azeotropic mixture while adding the solvent thus maintaining constant the volume of the mixture), at a temperature not exceeding +60° C. and under reduced pressure, will provide the crystallized product or when the most of the water will be removed or on cooling depending on the used solvent.

Conversely, for those cases where the Form A is obtained by direct crystallization of the crude disodium salt, its aqueous solution is taken up with an appropriate water-miscible organic solvent, at a temperature ranging from +5° C. to +60° C., under stirring. In order to assure the proper water activity in the crystallization mixture two approaches can be used, the first one involves water distillation until a determined volume followed by the addition of a measured volume of the organic solvent. The second approach consists of the addition of an organic solvent, forming an azeotropic mixture with water, and the distillation (solvent replacement distillation) of the mixture until the appropriate water concentration is reached (as determined for instance by Karl-Fischer test). Crystallization of the Form A will occur on stirring at a temperature from +5° C. to +60° C. or on slow cooling to a temperature depending on the concentration of the product and the solvent used. In addition, the endpoint temperature at which the solvated crystalline form is harvested will depend upon the solubility curve in the water organic-solvent mixture used. For most of the solvents described herein and within the ratio water/organic solvent that allows the precipitation of the pentahydrate in a reasonable yield, the endpoint temperature is typically lower than +60° C. and is preferably between +60 and +25° C. Temperature between +60° C. and +40° C. are generally preferred during the anti-solvent addition, in order to avoid precipitation of sticky materials. The crystallization temperature is then reached by slow cooling. For most of the solvents herein described, a cooling rate slower than about 20°/min. is preferable, and more preferable is a cooling rate between 10°/min and 2°/min. Seeding may be necessary during the direct crystallization of the Form A. The seeding is typically done before the cloud point (the lower end of the metastable zone) is reached. Suitable organic solvents used for the processes described are water miscible organic solvents, preferably pharmaceutically acceptable solvents of Class 2 or Class 3 (as defined in ICH Topic Q3C "Note for guidance on impurities: residual solvents", Step 4, July, 1997).

Preferable solvents are: acetone, methyl-ethyl ketone, 1-propanol, 2-propanol, ethanol, tetrahydrofurane. Procedures involving the two steps preparation (first precipitation followed by re-crystallization or phase equilibration) of the Form A are preferable over its direct crystallization from the crude disodium salt, often this preference being due to the higher chemical purity obtained.

In all cases, a particular attention should be given to the isolation and drying of Form A. Washings of the cake after filtration or of the panel during centrifugation with dry organic solvents should be avoided. Drying under high vacuum or at temperature higher than 50° C. for long times, should be avoided.

Representative not limiting examples of preparations of Andolast disodium penta-hydrate (Form A) are reported below.

Preparations by Phase Equilibration:

EXAMPLE 1

1.1 g of N-4-(1H-tetrazol-5-yl)phenyl-4-(1H-tetrazol-5-yl)benzamide disodium salt, (batch B/3610) were suspended in 3 mL of acetone-water mixture 1:1, at about 30° C., the resulting suspension was stirred at 25° C. for 24 hours. The precipitated solid was filtered and dried for 10 min. under vacuum, about 1 g of white powder was obtained, KF 19.35%; XRPD, FT-Raman and FT-IR spectra are reported in FIG. 11a-c.

EXAMPLE 2

25.0 g of N-4-(1H-tetrazol-5-yl)phenyl-4-(1H-tetrazol-5-yl)benzamide disodium salt, (batch B/3610) were suspended in 75 mL of isopropanol-water mixture 1:1, at about 30° C., the resulting suspension was stirred at 25° C. for 24 hours. The solid was isolated by filtration and dried at r.t. for 120 min. under air flow, about 25 g of white powder were obtained, KF 19.26%, XRPD, FT-Raman and FT-IR spectra are reported in FIGS. 12a-c.

EXAMPLE 3

600 g of N-4-(1H-tetrazol-5-yl)phenyl-4-(1H-tetrazol-5-yl)benzamide disodium salt, (batch B/7081) were suspended in 1850 mL of isopropanol-water mixture 1:1, at about 30° C., the resulting suspension was stirred at 25° C. for 24 hours. Then filtration and dying at 40° C./air for 62 hours afforded 542 g (90.3% w/w) of white powder. KF: 19.6%; XRPD, FT-Raman and FT-IR spectra were consistent with the corresponding ones previously reported in FIG. 11a-c and FIG. 12a-c.

EXAMPLE 4

2400 g of N-4-(1H-tetrazol-5-yl)phenyl-4-(1H-tetrazol-5-yl)benzamide disodium salt, (batch B/7081) were suspended in 7000 mL of isopropanol-water mixture 1:1, at about 30° C., the resulting suspension was stirred at 25° C. for 26 hours. Filtration and dying at 40° C./air for 62 hours afforded 2176 g (90.6 % w/w) of white powder. KF: 19.96%; XRPD, FT-Raman and FT-IR spectra were consistent with the corresponding ones previously reported in FIG. 11a-c and FIG. 12a-c.

Preparations by Re-Crystallization:

EXAMPLE 5

5 g of N-4-(1H-tetrazol-5-yl)phenyl-4-(1H-tetrazol-5-yl) benzamide disodium salt, (batch B/7081) were dissolved, by slightly heating at about 40° C., in 50 mL of water. To this solution, 750 mL of n-propanol were added drop wise in about 5 minutes, the obtained solution was stirred between 30° C. and 25° C. for 1.5 hours, after this time a solid started to appear. The suspension was stirred at 25° C. overnight. The solid was filtered, washed with a n-propanol-water mixture (15:1) and dried overnight at 40° C./air, 4.90 g (79%) of white fine powder were obtained. KF 19.55%, XRPD, FT-Raman and FT-IR spectra are reported in FIGS. 13a-c.

EXAMPLE 6

5.12 g of N-4-(1H-tetrazol-5-yl)phenyl-4-(1H-tetrazol-5-yl)benzamide disodium salt, (batch B/7081) were dissolved by slightly heating at about 40° C., in 50 mL of water. To this solution, 750 mL of acetone were added drop wise in about 30 seconds, the obtained solution was stirred between 30° C. and 25° C. for 5 minutes, after this time a flocky solid starts to appear. The suspension is stirred at 25° C. for further 2 hours. The solid is filtered, washed with an acetone-water mixture (15:1) and dried overnight at 40° C./air, 5.76 (91%) of white fine powder are obtained. KF 19.61%, XRPD, FT-Raman and FT-IR spectra were consistent with the ones reported in FIGS. 13a-c.

EXAMPLE 7

1.0 g of N-4-(1H-tetrazol-5-yl)phenyl-4-(1H-tetrazol-5-yl)benzamide disodium salt, (batch B/7081) were dissolved, by slightly heating at about 60° C., in 4 mL of water. To this solution, 12 mL of acetone were added without any precipitation. About 100 mg of previously obtained Form A were suspended in 0.5 mL of water-acetone 1:3 mixture, the suspension was heated to 60° C. and added drop wise to the clear solution. A white powder precipitates without sticking to the container wall. The suspension was cooled within 25 minutes to r.t. and 12 mL of acetone were added within 1 hours, a well stirrable suspension was obtained. The suspension was stirred at r.t. for about 2 hours then filtered (in this case filtration is easier that in example 6), dried overnight at 40° C./air; 1.18 g of white powder are obtained. KF 19.86%; XRPD, FT-Raman and FT-IR spectra were consistent with the ones reported in FIGS. 13a-c. The obtained product was analyzed by light microscopy, it consisted of particles of a diameter up to 200 µm, small particles (max diameter around 10 µm) were present in a negligible amount.

It is to point out that comparing the FT-IR spectra of Form A, for example as reported in FIG. 11c or FIG. 12c, with the FT-IR spectra of previous batches of hydrated mixtures, for example as reported in FIG. 6a or FIG. 6b for batches B/7080 and B/7081, it appears a consistent and striking difference in the region of the spectra 460-750 $cm^{-1}$.

Though the several undefined hydrated mixture displays undistinguishable FT-IR spectra (region 1800-460 $cm^{-1}$) the pentahydrate FT-IR spectrum displays a consistent and characteristic pattern of signals in the region 460-750 $cm^{-1}$.

The above examples highlight how Form A can be consistently obtained under controlled conditions either by phase equilibration or re-crystallization independently upon the scale, the preferred solvent used and the starting material batch.

For those pharmaceutical formulations where Andolast disodium Form A is used as powder for inhalation the PSD of the drug substance is critical to the performance of the drug product, due to bioavailability and delivery dose issues as discussed above. Any milling, micronizing or other particle size reduction methods known in the art can be used to obtain Form A in the desired size range as set forth above; however jet-mill procedures have been proved to be superior to other methods to achieve the particle size limits critical for drug substances to be used as dry powder for inhalation. It is well known in the art that the best performance of a jet-mill apparatus is obtained when the material to be micronized is characterized by rather large particles.

Form A can be easily prepared in the appropriate particle size, suitable for an optimal and consistent micronization step performance, either using the phase conversion preparation or obtaining it by re-crystallization. In both the cases, large particles suitable for an optimal micronization can be obtained by heating fast the suspension of the Form A at an appropriate temperature and then slowly cooling the suspension to r.t., to dissolve fines during the heating and to increase the size of the particles during the cooling.

Form A: Physical and Mechanical Characteristics

In the paragraphs reported below a non limiting selection of physical characteristics that endow Form A of suitable physical properties for formulation of drug products in general and particularly of those destined to inhalation are listed.

The list of improved physical and mechanical characteristics reported below is intended at documenting representative examples of advantages Form A is endowed with over the undefined hydrated forms obtained according to uncontrolled conditions. The list of advantages and improved characteristics herein reported is not intended to limit the advantages of using Andolast disodium salt Form A to those herein reported.

Stability to moisture: the physical stability of Form A is surprisingly good. Storage of Form A in humidity chambers at R.H. from 12% to 85%, at room temperature, for 9 days (see Example 8), did not alter the water content of any sample, neither the solid form.

EXAMPLE 8 samples of Form A were stored, as open samples, in an humidity controlled chamber for 9 days, in Table 5 water content (KF), XRPD and FT-Raman spectra at the end-point of the experiment are reported vs. R.H.

TABLE 5

| RH (%) | KF (%) | FT-Raman | XRPD |
|---|---|---|---|
| 12 | 19.26 | Complies with Form A | Complies with Form A |
| 22 | 19.36 | Complies with Form A | Complies with Form A |
| 32 | 19.34 | Complies with Form A | Complies with Form A |
| 53 | 19.35 | Complies with Form A | Complies with Form A |
| 65 | 19.25 | Complies with Form A | Complies with Form A |
| 75 | 19.22 | Complies with Form A | Complies with Form A |
| 85 | 19.43 | Complies with Form A | Complies with Form A |

Analogous experiments carried out with the several batches of the previously described undefined mixture of lower hydrates highlighted a strong absorption of water but leading to different water content depending upon the R.H., the time of exposure and the starting material.

All the materials (lower hydrates) observed after exposure to R.H. of at least 32% were converted with the time into the pentahydrate, the amount of the pentahydrate formed being depending upon the time of exposure, the R.H. and the starting material.

ICH accelerated stability testing for Form A confirmed its stability (physical form and chemical stability).

This surprising stability to moisture of Form A is also confirmed by DVS experiments. In the scanning mode, water is only lost when about 0% R.H. is reached. Moisture sorption/desorption behavior for the pentahydrate is reported in Example 9 (FIG. 14).

EXAMPLE 9

Water vapor sorption/desorption was analyzed using Surface Measurement System Ltd. DVS-1 apparatus. The sample was allowed to equilibrate at 50% R.H. before starting a predefinite humidity program, scanning with 5% ΔR.H. $hour^{-1}$ and with several "isohumid" equilibration periods (see FIG. 14 for details). The water content of the sample used for DVS was calculated on the basis of KF analysis, while crystalline form was assessed by FT-Raman spectroscopy. The DVS plots of water content vs. R.H. and R.H. vs. time are reported for Andolast disodium pentahydrate (Form A) in FIG. 14. It can be seen from the DVS plot that substantial desorption starts only at almost 0% RH. Based on this dynamic measurement, the pentahydrate shows a remarkable ability in withholding its water, resulting in a pronounced physical stability of the solid.

Stability to Temperature and Mechanical Mill

Stability of Andolast disodium Form A to temperature and mechanical milling conditions is proved by the following example:

EXAMPLE 10 about 1 g of Andolast disodium salt Form A was stored, as open sample, for 1 day at 50° C. The product was then milled for 10 min. at 24 s−1 in a ball swing mill. A sample was then analyzed by KF and FT-Raman spectroscopy. KF was 19.53% and Raman spectra confirmed no crystalline change occurred.

Accordingly, Andolast disodium Form A is a not hygroscopic solid, surprisingly stable to several humidity conditions in a temperature range acceptable for ordinary storage conditions. In addition its stability allows both chemical manufacturing and pharmaceutical manufacturing process consistency and reproducibility under conditions more viable and less expensive when compared to those used for highly hygroscopic solids. Form A stability under mechanical stress presents advantages not only for milling operations but also for all the process operations, including isolation (i.e. filtration and drying), handling of the bulk product (such as grinding, sieving), and operations dealing with its formulation like blending, compaction and compression. Form A is the only one able to guarantee a well defined and consistent crystalline form for hydrated Andolast disodium salt.

Stability and Performance to Micronization Conditions

As previously mentioned, to obtain powders where the most of particles are within the size range 1.0-3.0 μm is of critical importance in the development of an active substance for preparation of formulations intended for administration by inhalation. The term "particle size" as used herein refers to particle size measuring techniques well known in the art, such as laser light scattering. With the term "particle size distribution" (PSD) it is intended the particle size distribution curve as measured by these techniques, typically characterized by the $D_x$ particle size, where x is typically 10, 50 and 90. The $D_{90}$ particle size is a particle size such that 90% of the particles are smaller than the $D_{90}$ particle size, the meaning of $D_{10}$ and $D_{50}$ can be deduced consequently. PSD suitable for using Andolast disodium Form A in dry powder and pressurized HFA aerosols for inhalation are characterized by $D_{90}$: 10-15 μm, $D_{50}$: 2-4 μm , $D_{10}$: 01.-1.5 μm, more preferably is a PSD characterized by $D_{90}$: 4-6 μm, $D_{50}$: 2-3 μm , $D_{10}$: 05.-1.5 μm.

Any micronization or other particle size reduction methods known in the art can be used to obtain Form A in this desired PSD. Jet mill micronization has been proved superior to other methods to achieve the particle size limits, critical for the drug substances delivery in the respiratory tract, for a wide number of drug substances since it allows to obtain small particles with the lowest possible energy delivered to the micronization system. According to the jet mill technology the powder particles are fed into a flat cylindrical milling chamber tangentially through a venture system by pressurized air or nitrogen. The micronizing effect takes place by the collision between the slower incoming particles and those already accelerated in the spiral path. Centrifugal forces retain the larger particles at the periphery of the milling chamber, while the micronized particles exit from the centre of the chamber. The PSD is controlled by pressure and feed rate.

Previously, it was shown how Andolast disodium salt in an undefined hydrated form displayed changes in the XRPD spectra during jet mill micronization performed for achieving the PSD preferred for pharmaceutical formulation.

In Example 11 it is reported how Form A can be successfully micronized using conditions identical to the ones used for the micronization of the batch B/7081 (see FIGS. 7a and 7b for XRPD spectra) without altering XRPD and spectroscopic characteristics (Ft-Raman and FT-IR), thus proving Form A stability and crystalline form consistency also after the micronization step affording the suitable drug substance for preparing dry powder and pressurized HFA aerosols formulations for inhalation.

EXAMPLE 11

Andolast disodium form A is micronized, without cooling, using an MC Jet Mill apparatus, and nitrogen as carrier gas, at 12 bar and with a feeding rate of about 10 g/30 sec.

The preferred PSD is obtained using this conditions. Air with moisture can be used instead of nitrogen.

The micronized material was analyzed by XRPD, FT-IR and FT-Raman spectroscopy, no changes were observed in comparison to the starting material (not-micronized), as appears comparing FIGS. 15a,c spectra with the corresponding ones in FIGS. 13a,c.

Representative PSD obtained after jet mill micronization of Andolast disodium salt Form A are reported for two different preparations in Table 6.

TABLE 6

| Batch Prepared according to: | $D_{10}$ (μM) | $D_{50}$ (μM) | $D_{90}$ (μM) |
|---|---|---|---|
| Example 3 | 1.21 | 2.93 | 5.62 |
| Example 4 | 0.83 | 2.51 | 5.83 |

Moreover, the particles obtained by micronizing the Form A are characterized by a more regular shape in comparison to the ones obtained by micronization of the previous undefined hydrated material as highlighted by scanning electronic microscopy experiments, as shown in FIG. 16.

Advantages in Formulation

As discussed below Andolast disodium salt as Form A can be formulated according to several pharmaceutical compositions. In this paragraph aerosol performance of the new crystalline form is compared to that of the previous material as far as a dry powder formulation for inhalation is concerned. The pharmaceutical formulation herein used for comparison is the same that was reported in U.S. Pat. No. 5,976,576 (Example 1); the advantages in using Form A can be easily recognized both in terms of Metered Dose (MD), Delivered Dose (DD), Fine Particle Dose (FPD) and Fine Particle Fraction % (FPF %.) by using the MSLI (Multi Step Liquid Impinger) technique (see Table 8). In the same experiments a conventional capsules inhaler device was used and the formulated products were filled in hard gelatine capsules as described in U.S. Pat. No. 5,976,576; as representative batches micronized material obtained at Example 3 and micronized B/7080 were used as Form A representative batch and previous material representative batch respectively. In Table 7 the PSD of the two batches are compared to point out the equivalence of the two materials in terms of PSD.

TABLE 7

| Batch | $D_{10}$ (μM) | $D_{50}$ (μM) | $D_{90}$ (μM) |
|---|---|---|---|
| Micronized Form A obtained according to Example 3 | 1.21 | 2.93 | 5.62 |
| Micronized B/7080 | 0.64 | 1.71 | 4.76 |

TABLE 8

| Batch | Water Content (%) | Dose (mg) | MSLI | MD (mg) | DD (mg) | FPD (mg) | FPF (%) | MMAD (μm) |
|---|---|---|---|---|---|---|---|---|
| Form A obtained at Example 3 | 19.6 | 8 | 1 | 8.46 | 7.47 | 2.58 | 35 | 3.6 |
| | | | 2 | 8.33 | 7.33 | 1.97 | 27 | 3.9 |
| | | | 3 | 8.49 | 7.71 | 2.18 | 28 | 3.8 |
| | | | 4 | 8.60 | 7.43 | 2.20 | 30 | 3.8 |
| | | | 5 | 8.31 | 7.25 | 1.96 | 27 | 3.8 |
| | | | 6 | 8.67 | 7.54 | 2.07 | 27 | 4.0 |
| | | | Mean | 8.48 | 7.46 | 2.16 | 29 | 3.8 |
| B/7080 | 3.8 | 8 | 1 | 7.60 | 6.66 | 0.96 | | 5.3 |
| | | | 2 | 7.29 | 5.96 | 0.99 | | 5.2 |
| | | | 3 | 7.61 | 6.77 | 1.21 | | 5.1 |
| | | | 4 | 7.85 | 7.01 | 1.01 | | 5.4 |
| | | | 5 | 7.29 | 6.57 | 1.23 | | 5.1 |
| | | | 6 | 7.65 | 6.81 | 1.30 | | 5.1 |
| | | | Mean | 7.55 | 6.63 | 1.12 | 17 | 5.2 |

In Table 8 the better aerosol performance of Form A in comparison to the previous material in terms of MD, DD, FPD as well as FPF% is reported. Considerations about particle size equivalence and pharmaceutical composition equivalence between the two materials highlight how the better performance of the formulated new form is due to intrinsic crystal characteristics.

Improvements also in other characteristics (flow, adhesion properties) of the previous pharmaceutical composition, when using the new crystalline form, can be highlighted by considering that instead of the active ingredient/excipient ratio of 1:1 as reported in U.S. Pat. No. 5,976,576 (example 1), this ratio can be increased when using Form A, without significantly altering the aerosol performance of the pharmaceutical composition in terms MD, DD, FPD and FPF%, as appears from data reported in Table 9, where data are reported for the same micronized Form A batch as above, formulated with the same excipient as reported in U.S. Pat. No. 5,976,576 (example 1), but increasing the ratio of the active ingredient/excipient up to 2:1.

TABLE 9

| Ratio | Dose | MSLI | MD (mg) | DD (mg) | FPD (mg) | FPF (%) |
|---|---|---|---|---|---|---|
| 2:1 Andolast:Excipients | 16 mg | 1 | 15.2 | 13.6 | 4.37 | 32.2 |
| | | 2 | 15.2 | 13.6 | 4.06 | 29.9 |
| | | 3 | 15.5 | 13.8 | 4.16 | 30.2 |
| | | Mean | 15.3 | 13.6 | 4.20 | 30.9 |

Pharmaceutical Compositions

Andolast disodium salt in crystalline Form A may be administered on its own, or as a pharmaceutical composition comprising Andolast disodium salt in crystalline Form A in combination with a pharmaceutically acceptable diluent, adjuvant and/or carrier. Therefore is provided as a further feature of the invention a pharmaceutical composition comprising Andolast last disodium salt in crystalline Form A in combination with a pharmaceutically acceptable diluent, adjuvant and/or carrier.

Pharmaceutical compositions of Andolast disodium salt in crystalline Form A can be adapted to any suitable route of administration, including without limitation: oral, parenteral, topical and by inhalation. These compositions comprise Andolast disodium salt in crystalline Form A in a pharmacological effective amount, in combination with one or more excipients appropriate to the physical form used and consistent with the desired route of administration.

Oral dosage form of such compositions preferably comprise one or more excipients selected from the group of diluents, disintegrants, binding agents, wetting agents anti-adherent agents. Other excipients such as colorants, flavours and sweeteners are known in the pharmaceutical art and can be used in compositions of the invention. Preferably these oral dosage forms are administered as tablets or capsules.

Preferred formulations of the invention are those where Andolast disodium salt crystalline Form A, are administered by oral inhalation, particularly preferred formulations are dry powder formulation and pressurized aerosols wherein HFAs are the administration vehicles.

For inhalation, the crystalline Andolast disodium salt pentahydrate (Form A) is administered by means of a dry powder inhaler. The inhaler maybe a single or a multi dose inhaler, and may be a breath actuated dry powder inhaler.

Pharmaceutical formulations for inhalation can be prepared by mixing the micronized Andolast disodium salt pentahydrate (Form A), with carrier substances and other excipients such as flavours and sweeteners.

The invention claimed is:

1. N-4-(1H-tetrazol-5-yl)phenyl-4-(1H-tetrazol-5-yl)benzamide disodium salt pentahydrate, Form A, characterized by the following X-ray powder diffraction pattern expressed in terms of 2θ, d-spacings, and relative intensities, when CuKa radiation is used

| 2θ | d-value (Å) | Intensity % |
|---|---|---|
| 14.45 | 6.10 | 23 |
| 22.10 | 4.02 | 64 |
| 22.82 | 3.89 | 45 |
| 23.63 | 3.76 | 100 |
| 24.17 | 3.68 | 41 |
| 27.10 | 3.29 | 58 |
| 27.42 | 3.25 | 31 |
| 28.59 | 3.12 | 22 |
| 30.28 | 2.95 | 39 |
| 34.06 | 2.63 | 21. |

2. N-4-(1H-tetrazol-5-yl)phenyl-4-(1H-tetrazol-5-yl)benzamide disodium salt pentahydrate, Form A, according to claim 1 further characterized by the following FT-IR spectrum.

3. N-4-(1H-tetrazol-5-yl)phenyl-4-(1H-tetrazol-5-yl)benzamide disodium salt pentahydrate, Form A, according to claim 1 further characterized by the following FT-Raman.

4. A method of preparing a medicament comprising using Form A, as defined in claim 1, wherein the drug substance is N-4-(1H-tetrazol-5-yl)phenyl-4-(1H-tetrazol-5-yl)benzamide disodium salt.

5. A pharmaceutical composition comprising a therapeutically effective amount of N-4-(1H-tetrazol-5-yl)phenyl-4-(1H-tetrazol-5-yl)benzamide disodium salt pentahydrate, as defined in claim 1, in mixture with at least one pharmaceutically acceptable excipient, diluent or carrier.

6. A process for preparing the Form A as defined in claim 1, the process comprising converting an hydrate mixture of N-4-(1H-tetrazol-5-yl)phenyl-4-(1H-tetrazol-5-yl)benzamide disodium salt into the pentahydrate, form A, by slurry conversion.

7. A process according to claim 6, where the slurry conversion is obtained in a water-organic solvent mixture at temperature ranging from +5° C. to 60° C.

8. A process according to claim 6, wherein the organic solvent comprises a solvent selected from: acetone, 2-propanone, 1-propanol, 2-propanol, ethanol, tetrahydrofuran or a mixture of these solvents.

9. A process for preparing the crystalline Form A as defined in claim 1, the process comprising crystallizing N-4-(1H-tetrazol-5-yl)phenyl-4-(1H-tetrazol-5-yl) benzamide disodium salt pentahydrate, from a water-organic solvent mixture at temperature ranging from +5° C. to 60° C.

10. A process according to claim 9, wherein the organic solvent comprises a solvent selected from the group: acetone, 2-propanone, 1-propanol, 2-propanol, ethanol, tetrahydrofuran or a mixture of these solvents.

11. A process according to claim 9, wherein the precipitation of Form A is obtained by seeding with preformed form A, at a temperature of about 60° C.

12. A process according to claim 6, wherein the drying of Form A is done at temperature below 70° C. and at a pressure ranging from 1 to 200 mmHg.

13. A process according to claim 6, wherein the drying of Form A is done at temperature ranging from 10 to 30° C. and at a pressure ranging from $1.10^{-5}$ to $1.10^{-2}$ mmHg.

14. A process according to claim 6, wherein the drying of Form A is done at temperature ranging from 10 to 80° C. and at a R.H. ranging from 50 to 70%.

15. N-4-(1H-tetrazol-5-yl)phenyl-4-(1H-tetrazol-5-yl)benzamide disodium salt pentahydrate, Form A, according to claim 1, further characterized by the following X-ray powder diffraction pattern expressed in terms of 2θ, d-spacings, and relative intensities, when CuKa radiation is used

| 2θ | d-value (Å) | Intensity % |
|---|---|---|
| 14.45 | 6.10 | 23 |
| 18.39 | 4.82 | 14 |
| 22.10 | 4.02 | 64 |
| 22.82 | 3.89 | 45 |
| 23.63 | 3.76 | 100 |
| 24.17 | 3.68 | 41 |
| 25.60 | 3.48 | 15 |
| 25.90 | 3.44 | 10 |
| 26.71 | 3.34 | 10 |
| 27.10 | 3.29 | 58 |
| 27.42 | 3.25 | 31 |
| 28.59 | 3.12 | 22 |
| 30.28 | 2.95 | 39 |
| 30.56 | 2.92 | 14 |
| 30.83 | 2.90 | 10 |
| 31.72 | 2.82 | 10 |
| 32.94 | 2.72 | 13 |
| 33.25 | 2.69 | 10 |
| 34.06 | 2.63 | 21 |
| 35.56 | 2.52 | 11 |
| 36.82 | 2.44 | 10 |
| 38.88 | 2.31 | 12. |

* * * * *